(12) United States Patent
Dahlhauser

(10) Patent No.: US 7,906,287 B2
(45) Date of Patent: Mar. 15, 2011

(54) METHODS OF SCREENING NUCLEIC ACIDS FOR SINGLE NUCLEOTIDE VARIATIONS

(75) Inventor: Paul A. Dahlhauser, Nashville, TN (US)

(73) Assignee: Insight Genetics, Inc., Nashville, TN (US)

( * ) Notice: Subject to any disclaimer, the term of this patent is extended or adjusted under 35 U.S.C. 154(b) by 20 days.

(21) Appl. No.: 12/152,512

(22) Filed: May 14, 2008

(65) Prior Publication Data

US 2009/0053715 A1 Feb. 26, 2009

Related U.S. Application Data

(60) Provisional application No. 60/917,763, filed on May 14, 2007.

(51) Int. Cl.
C12Q 1/68 (2006.01)
C07H 21/02 (2006.01)
C07H 21/04 (2006.01)

(52) U.S. Cl. .......................... 435/6; 536/23.1; 536/24.3
(58) Field of Classification Search ..... 435/6; 536/23.1, 536/24.3
See application file for complete search history.

(56) References Cited

U.S. PATENT DOCUMENTS

| | | | |
|---|---|---|---|
| 5,002,867 A | | 3/1991 | Macevicz |
| 5,202,231 A * | | 4/1993 | Drmanac et al. .............. 435/6 |
| 5,354,656 A * | | 10/1994 | Sorge et al. .............. 435/6 |
| 5,391,480 A | | 2/1995 | Davis et al. |
| 5,459,039 A * | | 10/1995 | Modrich et al. .............. 435/6 |
| 5,556,750 A * | | 9/1996 | Modrich et al. .............. 435/6 |
| 5,698,400 A * | | 12/1997 | Cotton et al. .............. 435/6 |
| 5,702,894 A * | | 12/1997 | Modrich et al. .............. 435/6 |
| 5,710,028 A * | | 1/1998 | Eyal et al. .............. 435/91.1 |
| 5,736,373 A * | | 4/1998 | Hamilton .............. 435/194 |
| 5,744,306 A * | | 4/1998 | Murtagh et al. .............. 435/6 |
| 5,795,714 A | | 8/1998 | Cantor et al. |
| 5,861,482 A * | | 1/1999 | Modrich et al. .............. 530/350 |
| 5,869,245 A * | | 2/1999 | Yeung .............. 435/6 |
| 5,922,539 A * | | 7/1999 | Modrich et al. .............. 435/6 |
| 6,150,105 A * | | 11/2000 | Dahlhauser .............. 435/6 |
| 6,297,018 B1* | | 10/2001 | French et al. .............. 435/6 |
| 6,361,947 B1* | | 3/2002 | Dong et al. .............. 435/6 |
| 6,475,736 B1* | | 11/2002 | Stanton, Jr. .............. 435/6 |
| 6,610,486 B1* | | 8/2003 | Dahlhauser .............. 435/6 |
| 6,632,611 B2* | | 10/2003 | Su et al. .............. 435/6 |
| 6,969,589 B2* | | 11/2005 | Patil et al. .............. 435/6 |
| 6,972,174 B2* | | 12/2005 | Xue et al. .............. 435/6 |
| 7,108,976 B2* | | 9/2006 | Jones et al. .............. 435/6 |
| 7,175,982 B1 | | 2/2007 | McCarthy |
| 7,208,278 B2* | | 4/2007 | Chen et al. .............. 435/6 |
| 7,470,517 B2* | | 12/2008 | Cantor et al. .............. 435/6 |
| 7,579,155 B2* | | 8/2009 | Taylor et al. .............. 435/6 |
| 2002/0197632 A1* | | 12/2002 | Moskowitz .............. 435/6 |
| 2003/0036069 A1* | | 2/2003 | Su .............. 435/6 |
| 2003/0049628 A1* | | 3/2003 | Kambara et al. .............. 435/6 |
| 2003/0051270 A1* | | 3/2003 | Kmiec et al. .............. 800/21 |
| 2003/0104464 A1 | | 6/2003 | Berlin |
| 2003/0186262 A1 | | 10/2003 | Cailloux |
| 2003/0219769 A1* | | 11/2003 | Olson et al. .............. 435/6 |
| 2008/0206748 A1* | | 8/2008 | Olson et al. .............. 435/6 |
| 2009/0053715 A1* | | 2/2009 | Dahlhauser .............. 435/6 |

FOREIGN PATENT DOCUMENTS

| | | |
|---|---|---|
| AU | 57805/99 | 8/1999 |
| AU | 2008254986 | 5/2008 |
| CA | 2340306 | 8/1999 |
| CA | 2687218 | 5/2008 |
| CN | 99812395.1 | 8/1999 |
| CN | 200880024607.6 | 5/2008 |
| EP | 0412883 | * 2/1991 |
| EP | 99945120.6 | 8/1999 |
| EP | 08754474.8 | 5/2008 |
| IN | 7684/DELNP/2009 | 5/2008 |
| JP | 2000-566473 | 8/1999 |
| JP | 2010-508416 | 5/2008 |

(Continued)

OTHER PUBLICATIONS

Colbert et al. High-Throughput Screening for Induced Point Mutations.Plant Physiology 126 :480484 (2001).*

(Continued)

Primary Examiner — Ethan Whisenant
(74) Attorney, Agent, or Firm — Ballard Spahr LLP

(57) ABSTRACT

Disclosed are methods and compositions for detecting variation in nucleic acids. The disclosed method compares the sequence of a nucleic acid of interest with the sequence of a reference nucleic acid to sensitively identify variations between the sequence of a nucleic acid of interest and the sequence of a reference nucleic acid. The disclosed method generally involves excision and replacement of selected nucleotides in nucleic acid strands hybridized to other strands. In the method, if the excised nucleotide was mismatched with the nucleotide in the other, hybridized strand, then the replacement nucleotide will not be mismatched. If the excised nucleotide was not mismatched with the nucleotide in the other, hybridized strand, then the excised nucleotide is not replaced. This difference allows detection of variation in the nucleic acid of interest. In some forms of the method, by replacing excised nucleotides with nuclease-resistant nucleotides, strands in which excised nucleotides are replaced will be resistant to nuclease digestion while strands in which excised nucleotides are not replaced will be sensitive to nuclease digestion. By exposing the hybridizing nucleic acids to nuclease following replacement of excised nucleotides, the strands in which excised nucleotides are not replaced can be destroyed by the nuclease while strands in which excised nucleotides are replaced can be preserved. The remaining strands can then be detected and whether the strand survived nuclease digestion can be noted. Strands that survive nuclease digestion are indicative of the presence of variation in the nucleic acid of interest.

46 Claims, 6 Drawing Sheets

FOREIGN PATENT DOCUMENTS

| JP | 2009-291508 | | 12/2009 |
|---|---|---|---|
| MX | 2001-001913 | | 8/1999 |
| RU | 2009146054 | | 5/2008 |
| WO | WO 95/00669 | * | 1/1995 |
| WO | WO 96/30545 | * | 10/1996 |
| WO | WO 97/35033 | * | 9/1997 |
| WO | PCT/US99/19007 | | 8/1999 |
| WO | WO 00/11222 | | 3/2000 |
| WO | PCT/US2008/006191 | | 5/2008 |

OTHER PUBLICATIONS

Hawkins et al., Rapid DNA mutation identification and fingerprinting using base excision sequence scanning. Electrophoresis 20 : 1171-1176 (1999).*
Hawkins et al. Base excision sequence scanning. Nature Biotechnology 15 : 803-804 (1997).*
Hsu et al., Detection of DNA point mutations with DNA mismatch repair enzymes. Carcinogenesis 15(8) : 1657-1662 (1994).*
Oleykowski et al., Mutation detection using a novel plant endonuclease. Nucleic Acids Research 26 (20) : 4597-4602 (1998).*
Pincas et al., High sensitivity EndoV mutation scanning through real-time ligase proofreading. Nucleic Acids Research 32 (19) : e148 (2004).*
Qiu et al., Mutation detection using SurveyorTM nuclease. BioTechniques 36 (4) : 702-707 (2004).*
Till et al., Large-scale discovery of induced point mutations with high-throughput TILLING. Genome Research 13: 324-330 (2003).*
Wilson et al., Incision Activity of Human Apurinic Endonuclease (Ape) at Abasic Site Analogs in DNA. J. Biol. Chem. 270 (27): 16002-16007(1995).*
Yeung et al., Enzymatic mutation detection technologies. Review Article. BioTechniques. 38(5) : 749-758 (2005).*
Yu et al., Tailed Primer Base Excision Sequence Scanning (TP-BESS) for Detection of Single Nucleotide Polymorphisms (SNPs). Plant Molecular Biology Reporter 19 : 49-54 (2001).*
Au et al. Escherichia coli mutY gene encodes an adenine glycosylase active on G-A mispairs. PNAS 86 :8877-8881 (1989).*
Hardeland et al., The versatile thymine DNA-glycosylase: a comparative characterization of the human, Drosophila and fission yeast orthologs. Nucleic Acids Research 31(9) :2261-2271 (2003).*
First Office Action w/English Translation mailed Nov. 21, 2003 (CN App No. 99812395.1 - national phase of PCT/US99/19007).
Response to First Office Action mailed Jun. 6, 2004 (CN App. No. 99812395.1 - national phase of PCT/US99/19007).
Second Office Action mailed May 25, 2007 (CN App. No. 99812395.1 - national phase of PCT/US99/19007).
Response to Second Office Action (CN App. No. 99812395.1 - national phase of PCT/US99/19007).
Certificate No. 416711, Patent No. ZL99812395.1 issued Aug. 6, 2008 (CN App. No. 99812395.1 - national phase of PCT/US99/19007).
Official Action Mailed Dec. 27, 2007 (CA Patent App No. 2,340,306 - national phase of PCT/US99/19007).
Response to Dec. 27, 2007 Official Action mailed Jun. 27, 2008 (CA Patent App No. 2,340,306 - national phase of PCT/US99/19007).
Official Action mailed Jun. 2, 2009 (CA Patent App No. 2,340,306 - national phase of PCT/US99/19007).
Response to Jun. 2, 2009 Official Action mailed Dec. 2, 2009 (CA Patent App No. 2,340,306 - national phase of PCT/US99/19007).
Official Action mailed Jul. 30, 2010 (CA Patent App No. 2,340,306 - national phase of PCT/US99/19007).
Office Action mailed Nov. 16, 2007 (EP Patent App No. 99945120.6 - national phase of PCT/US99/19007).
Response to Nov. 11, 2007 Office Action mailed Jun. 16, 2008 (EP App No. 99945120.6 - national phase of PCT/US99/19007).
Office Action mailed Apr. 27, 2010 (EP Patent App No. 99945120.6 - national phase of PCT/US99/19007).
Office action mailed Jun. 22, 2009 (JP Patent App. No. 2000-566473 - National Phase of PCT/US99/19007).
Response to Jun. 22, 2009 Office Action mailed Dec. 22, 2009 (JP Patent App. No. 2000-566473 - National Phase of PCT/US99/19007).
Official Action mailed Mar. 9, 2010 (JP Patent App. No. 2000-566473 - National Phase PCT/US99/19007).
Notice of Allowance mailed Jul. 24, 2004 (Mexican App. No. 2001-001913).
Babon JJ, McKenzie M, Cotton RG. Mutation detection using fluorescent enzyme mismatch cleavage with T4 endonuclease VII. Electrophoresis 20(6):1162-70 (1999).
Bi and Stanbrook Detection of known mutation by proof-reading PCR. Nucleic Acids Research, 26(12)3073-3075 (1998).
Brow MA, Oldenburg MC, Lyamichev V, et al. Differentiation of bacterial 16S rRNA genes and intergenic regions and Mycobacterium tuberculosis katG genes by structure-specific endonuclease cleavage. J Clin Microbiol;34(12):3129-37 (1996).
Chee et al., Science, 274:610 614 (1996).
Chen TJ, Boles RG, Wong LJ. Detection of mitochondrial DNA mutations by temporal temperature gradient gel electrophoresis. Clin Chem;45(8 Pt 1):1162-7 (1999).
Cotton RG, Rodrigues NR, Campbell RD. Reactivity of cytosine and thymine in single-base-pair mismatches with hydroxylamine and osmium tetroxide and its application to the study of mutations. Proc Natl Acad Sci U S A;85 (12):4397-401 (1988).
Fisher and Lerman. (Proc. Natl. Acad. Sci. U.S.A., 80:1579 1583 (1983).
Fodde R, Losekoot M. Mutation detection by denaturing gradient gel electrophoresis (DGGE). Hum Mutat;3(2):83-94 (1994).
Ganguly A, Prockop DJ. Detection of mismatched bases in double stranded DNA by gel electrophoresis. Electrophoresis 1995;16(10):1830-5.
Ganguly A, Rock MJ, Prockop DJ. Conformation-sensitive gel electrophoresis for rapid detection of single-base differences in double-stranded PCR products and DNA fragments: evidence for solvent-induced bends in DNA heteroduplexes. Proc Natl Acad Sci U S A;90(21):10325-9 (1993).
Hacia JG. Resequencing and mutational analysis using oligonucleotide microarrays. Nat Genet 21(1 Suppl):42-7 (1999).
Higgins G. et al. Competitive oligonucleotide single-base extension combined with mass spectrometric detection for mutation screening Biotechniques; 23(4):710-714 (1997).
Hovig E, Smith-Sorensen B, Brogger A, Borresen AL. Constant denaturant gel electrophoresis, a modification of denaturing gradient gel electrophoresis, in mutation detection. Mutat Res ;262(1):63-71 (1991).
Labeit S, Lehrach H, Goody RS. A new method of DNA sequencing using deoxynucleoside alpha-thiotriphosphates. DNA;5(2):173-7 (1986).
Labeit S, Lehrach H, Goody RS. DNA sequencing using alpha-thiodeoxynucleotides. Methods Enzymol;155:166-77 (1987).
Lipshutz et al., Biotechniques, 9(3):442 447 (1995).
Liu et al., Hum. Mol. Genet., 5(1):107 114 (1996).
Liu and Sommer, Biotechniques, 18(3):470 477 (1995).
Lu AL, Hsu IC. Detection of single DNA base mutations with mismatch repair enzymes. Genomics 1992;14(2):249-55.
Myers RM, Larin Z, Maniatis T. Detection of single base substitutions by ribonuclease cleavage at mismatches in RNA: DNA duplexes. Science 1985;230(4731):1242-6.
Nagamine CM, Chan K, Lau YF. A PCR artifact: generation of heteroduplexes. Am J Hum Genet 1989;45(2):337-9.
Nakamaye KL, Gish G, Eckstein F, Vosberg HP. Direct sequencing of polymerase chain reaction amplified DNA fragments through the incorporation of deoxynucleoside alpha-thiotriphosphates. Nucleic Acids Res 1988;16 (21):9947-59.
Newton et al. Analysis of any point mutation in DNA. The amplification refractory mutation system (ARMS); Nucleic Acids Res; 17(7):2503-2516 (1989).
Novack DF Casna NJ, Fischer SG, Ford JP. Detection of single base-pair mismatches in DNA by chemical modification followed by electrophoresis in 15% polyacrylamide gel. Proc Natl Acad Sci U S A; 83(3):586-90 (1986).

Oldenburg MC, Siebert M. New Cleavase Fragment Length Polymorphism method improves the mutation detection assay. Biotechniques 2000;28(2):351-7.

Orita M, Suzuki Y, Sekiya T, Hayashi K. Rapid and sensitive detection of point mutations and DNA polymorphisms using the polymerase chain reaction. Genomics 1989;5(4):874-9.

Pastinen T. et al. Multiplex, fluorescent, solid-phase minisequencing for efficient screening of DNA sequence variation. Clinical Chem; 42(9):1391-1397 (1996).

Pincas H, Pingle MR, Huang J, et al. High sensitivity EndoV mutation scanning through real-time ligase proofreading. Nucleic Acids Res 2004;32(19):e148.

Porter KW, Briley JD, Shaw BR. Direct PCR sequencing with boronated nucleotides. Nucleic Acids Res; 25(8):1611-7 (1997).

Rosenbaum, et al. "Temperature-gradient gel electrophoresis. Thermodynamic analysis of necleic acids and proteins in purified form and in cellular extracts", Biophysical Chemistry 26:235-246 (1987).

Sarkar, et al. "Dideoxy Fingerprinting (ddF): A Rapid and Efficient Screen for the Presence of Mutations", Genomics 13:441-443 (1992).

Winter E, Yamamoto F, Almoguera C, Perucho M. A method to detect and characterize point mutations in transcribed genes: amplification and overexpression of the mutant c-Ki-ras allele in human tumor cells. Proc Natl Acad Sci U S A 1985;82(22):7575-9.

Wu D. Y. Allele-specific enzymatic amplification of -globin genomic DNA for diagnosis of sickle cell anemia; PNAS USA; 86(8):2757-2760 (1989).

Xiao W, Oefner PJ. Denaturing high-performance liquid chromatography: A review. Hum Mutat 2001;17(6):439-74.

Youil R, Kemper B, Cotton RG. Detection of 81 of 81 known mouse beta-globin promoter mutations with T4 endonuclease VII—the EMC method. Genomics 1996;32:431-5.

Notification of Transmittal of International Preliminary Examination Report mailed Nov. 17, 2009 (International Application No. PCT/US99/19007).

International Search Report and Written Opinion mailed Oct. 1, 2000 (International Application No. PCT/US99/19007).

Notification of Transmittal of the International Search and Written Opinion mailed Nov. 14, 2008 (International Application PCT/US2008/006191).

Notification Concerning Transmittal of International Preliminary Report on Patentability mailed Nov. 17, 2009 (International Application PCT/US2008/006191).

Non-final Office Action mailed Jul. 29, 2002 (U.S. Appl. No. 09/717,793).

Response After Non-Final Action dated Oct. 18, 2002 (U.S. Appl. No. 09/717,793).

Notice of Allowance mailed Mar. 6, 2003 (U.S. Appl. No. 09/717,793).

Issue Notification mailed Aug. 7, 2003 (U.S. Appl. No. 09/717,793).

Notice of Allowabilty mailed Jun. 20, 2000 (U.S. Appl. No. 09/137,075).

Submission of Formal Drawings submitted w/payment of issue fee mailed Sep. 20, 2000 (U.S. Appl. No. 09/137,075).

Issue of Notification mailed Nov. 2, 2000 (U.S. Appl. No. 09/137,075).

Examiner First Report mailed Sep. 4, 2002 (AU Patent App. 57805/99 - National Phase of PCT/US99/19007).

Response to Examiner's First Report mailed May 11, 2004 (AU Patent App. 57805/99 -(National Phase of PCT/US99/19007).

Notice of Acceptance mailed may 14, 2004 (AU Patent App. 57805/99 -(National Phase of PCT/US99/19007).

Registration and Notice of Sealing AU Patent No. 774357 issued Oct. 7, 2004 - (AU Patent App. 57805/99 -(National Phase of PCT/US99/19007).

U.S. Appl. No. 09/137,075, filed Sep. 20, 1998, Dalhlhauser, P.

U.S. Appl. No. 09/717,793, filed Nov. 20, 2000, Dalhlhauser, P.

Response to Apr. 27, 2010 Office Action filed Nov. 5, 2010 (EP Application No. 99945120.6 - National Phase of PCT/US99/19007).

Response to Mar. 9, 2010 Official Action filed Sep. 9, 2010 in Japanese language w/English Translation of Claims (JP Application No. 2000-566473 - National Phase of PCT/US99/19007).

Office Action mailed May 11, 2010 (EP Application No. 08754474.8 - National Phase PCT/US2008/006191).

Response to May 11, 2010 Office Action filed Nov. 22, 2010 (EP Application 08754474.8 - National Phase of PCT/US2008/006191).

* cited by examiner

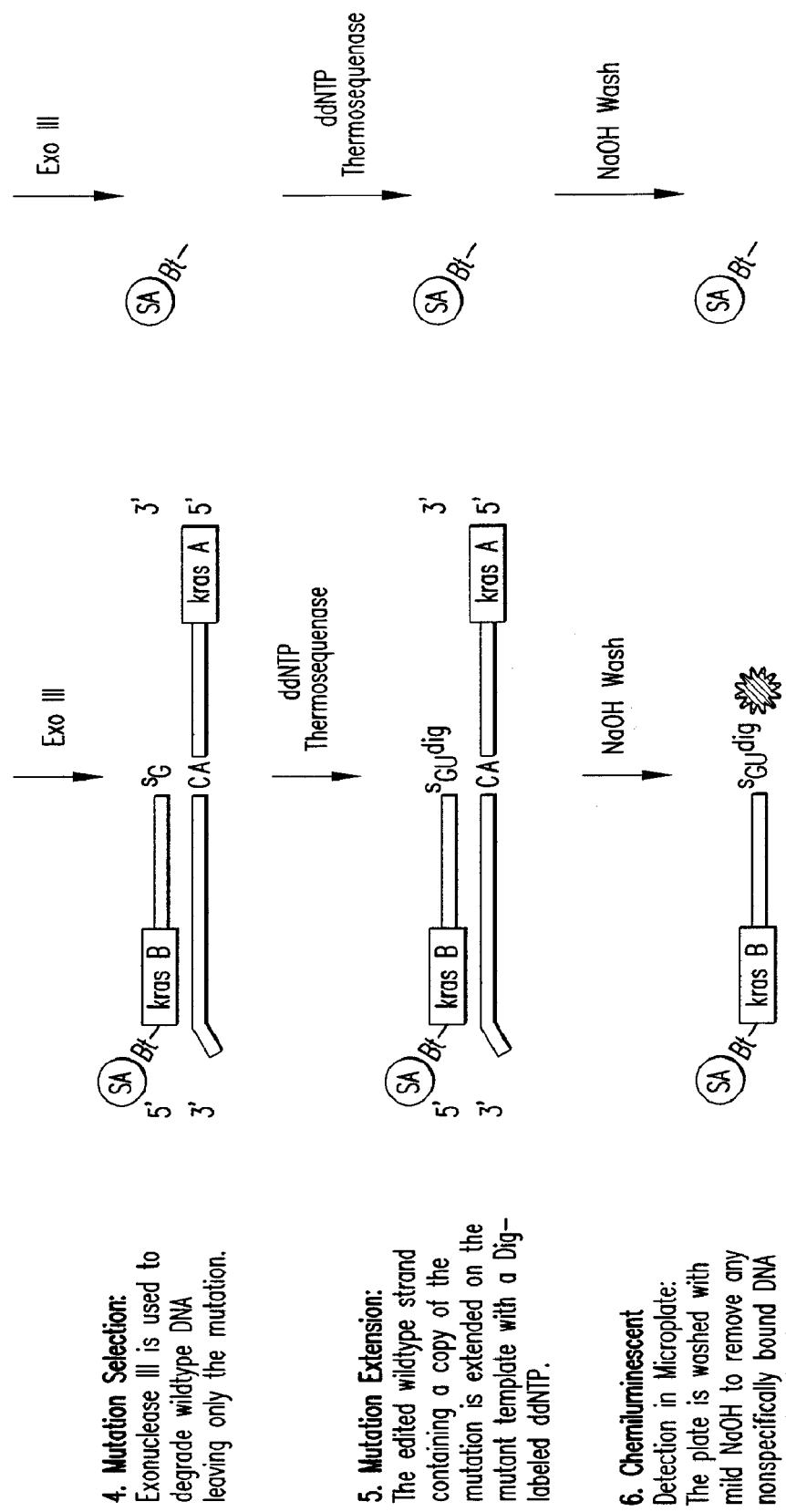

FIG.2B

4. Mutation Selection:
Exonuclease III is used to degrade wildtype DNA leaving only the mutation.

5. Mutation Extension:
The edited wildtype strand containing a copy of the mutation is extended on the mutant template with a Dig-labeled ddNTP.

6. Chemiluminescent Detection in Microplate:
The plate is washed with mild NaOH to remove any nonspecifically bound DNA followed by chemiluminescent detection of the digoxigenin label ddNTP.

```
        LamMM-KrasB                    kras A capture
5' FAM ATAGGCGTACTGGTGGAGTATTTATAAAGGTTTCTCTGAGGTGA-BT SEQ ID NO:1
                 CACCTCATAAATATTTCCAAAG  SEQ ID NO:2
                        Nick Linker LamMM-KrasB                    kras A capture
5' FAM ATAGGCGTACTGGTGGAGTATTT ATAAAGGTTTCTCTGAGGTGA-BT
                 CACCTCATAAACTATTTCCAAAG  SEQ ID NO:3
                        Gap C Linker
```

FIG.4

METHODS OF SCREENING NUCLEIC ACIDS FOR SINGLE NUCLEOTIDE VARIATIONS

CROSS-REFERENCE TO RELATED APPLICATIONS

This application claims the benefit of priority to U.S. Provisional Application No. 60/917,763, filed May 14, 2007. U.S. Provisional Application No. 60/917,763 is incorporated by reference herein in its entirety.

BACKGROUND

The efficacy of many drugs has been linked to specific mutations or polymorphisms in genes. The era of personalized genetic medicine has become a reality. Today doctors are prescribing drugs based on genetic information. Infectious disease doctors are prescribing drugs for the treatment of AIDS based on resistance mutations found in the human immunodeficiency virus isolated from the patient (Rhee S Y, et al. *Antimicrob Agents Chemother* 2004; 48(8):3122-6). Polymorphisms in the cytochrome p450 gene are being used to determine a patient's drug-metabolizer status (Ingelman-Sundberg M. *Trends Pharmacol Sci* 2004; 25(4): 193-200). Mutations in the epidermal growth factor receptor gene activate a substantial clinical response to the drug gefitinib in 10% of non-small cell lung cancer patients (Lynch T J, et al. *N Engl J Med* 2004; 350(21): 2129-39).

Additionally, the early detection and treatment of cancer significantly reduces suffering and death. In fact, most cancers are curable when detected early. Molecular analysis of genomic DNA to detect a small number of cancerous cells in body fluids is a promising approach to the early detection of cancer.

Tumors transiently shed cells into adjacent body fluids. Malignant cells from localized tumors have been detected in blood, sputum, urine and stool. Sensitive detection of these rare cells is difficult because of the large excess of normal cells in these body fluids. The molecular signal generated from the normal or wildtype DNA from these cells overwhelms or out competes the minor mutant fraction signal.

The number of diseases that are linked to gene mutations continues to increase as the sequence of the human genome is unraveled. Many technologies have emerged to positively select for these minor mutations such that their signal can be amplified over the wildtype. These technologies can be divided into two types; those that detect known mutations and those that detect unknown mutations.

The sensitive detection of a mutation at a known site in DNA is readily done with existing technologies. Allele specific primers can be designed to target a mutation at a known location such that its signal can be preferentially amplified over wildtype DNA. Unfortunately, this is not possible with unknown mutations that may occur at any position (base) in the target sequence. Most mutations in cancer genes are not located at defined positions. The kras gene is highly mutated in cancer. Mutations are clustered in hotspots at exon 12 and 13, but can occur throughout the gene.

Nucleic acid sequencing is the ultimate standard for detecting nucleotide variations. Nucleic acid sequencing is also well suited for detecting unknown mutations or polymorphisms that may occur at any base within a target nucleic acid segment. The chemistry of enzymatic DNA sequencing, the most commonly used method, has essentially remained the same since its conception (Sanger et al., Proc. Natl. Acad. Sci. U.S.A., 74, 5463 (1977)). However, it has limitations related to cost, read length, and detection of mutations. The art has been improved by technology that has allowed for its automation such as the introduction of fluorescent dyes, robotics and improved electrophoretic systems with automated detection. However, if genetic variations occur at a low frequency in the sample population, automation comes at a cost that is too high for most laboratories. Even in a manual mode, sequencing can be cost prohibitive because it is labor intensive. This limits its widespread use as a detection tool, especially when the variation occurs at a low frequency in the sample population being tested. Moreover, the read length is limited by the resolution power of electrophoretic separation. The detection of mutations by DNA sequencing is not always obvious, especially if it compromises less than 20% of the wildtype sequence.

DNA microarrays, also known as gene chips and oligonucleotide microarrays, have been gaining more main stream use for detecting both known and unknown variations Hacia J G. *Nat Genet.* 1999; 21(1 Suppl):42-7). They are particularly suited for high-density analysis of a particular genetic sequence usually from a small number of individuals. But, because of high equipment and manufacturing costs, it is not as suited for large-scale population screening of unknown variations. Chips are also extremely inefficient at detecting insertions and deletion mutations. Increasing the complexity of chips by 2 to 4 fold by adding oligonucleotides to detect these mutations is problematic. Also, microarrays, like sequencing, do not have adequate sensitivity to detect mutations that may be present as a minor fraction in a vast amount of wildtype DNA. Thus, the discovery and detection of genetic variations linked to drug efficacy is hindered by the inadequacies of current technology. Therefore, there is a need in the art for a simple inexpensive process to screen nucleic acids for unknown nucleotide variations prior to sequencing.

BRIEF SUMMARY

The methods disclosed herein relate to the field of detecting nucleotide variations in a nucleic acid. It is understood and herein contemplated that the methods disclosed herein allow for rapid and sensitive detection of rare mutations including mutations comprising single nucleotide variations in the presence of excess normal DNA.

Disclosed are methods and compositions for detecting variation in nucleic acids. The disclosed method compares the sequence of a nucleic acid of interest with the sequence of a reference nucleic acid to sensitively identify variations between the sequence of a nucleic acid of interest and the sequence of a reference nucleic acid. The disclosed method generally involves excision and replacement of selected nucleotides in nucleic acid strands hybridized to other strands. One of the nucleic acids strands in a hybridizing nucleic acid is, or is derived from, a nucleic acid of interest and the other nucleic acid strand the hybridizing nucleic acid is, or is derived from, a reference nucleic acid. This arrangement allows comparison of the sequence of the nucleic acid of interest with the sequence of the reference nucleic acid. In the method, if the excised nucleotide was mismatched with the nucleotide in the other, hybridized strand, then the replacement nucleotide will not be mismatched. If the excised nucleotide was not mismatched with the nucleotide in the other, hybridized strand, then the excised nucleotide is not replaced. This difference allows detection of variation in the nucleic acid of interest.

In some forms of the method, by replacing excised nucleotides with nuclease-resistant nucleotides, strands in which excised nucleotides are replaced will be resistant to nuclease digestion while strands in which excised nucleotides are not replaced will be sensitive to nuclease digestion. By exposing the hybridizing nucleic acids to nuclease following replacement of excised nucleotides, the strands in which excised nucleotides are not replaced can be destroyed by the nuclease while strands in which excised nucleotides are replaced can be preserved. The remaining strands can then be detected and whether the strand survived nuclease digestion can be noted. Strands that survive nuclease digestion are indicative of the presence of variation in the nucleic acid of interest.

In some forms of the method, the excised nucleotides are modified nucleotides that have been incorporated into a nucleic acid strand produced from a template nucleic acid. The template nucleic acid can be a nucleic acid of interest or a reference nucleic acid. The modified nucleotides can be incorporated at various frequencies, but most usefully at an average of once per synthesized strand. The differentiation of strands with mismatched and strands without mismatched excised nucleotides can be facilitated by limiting the type of modified nucleotide and/or the type of base used for the modified nucleotides. Thus, for example, use of modified nucleotides having only certain types of base means that nucleotides will only be excised at positions characterized by the types of bases used in the modified nucleotides. Such limited scope for the identity of nucleotides that can be excised allows limitations to be placed on the identity of the replacement nucleotides. Thus, for example, use of replacement nucleotides having types of bases other than the type of base on the modified nucleotides can allow replacement only of modified nucleotides that were mismatched with the hybridizing strand. In particularly useful forms of the method, modified nucleotides having a single type of base and replacement nucleotides collectively having the three other types of bases can be used. This allows identification of the type of nucleotide that is variant when a variant is detected.

In accordance with the purpose(s) of this invention, as embodied and broadly described herein, this invention, in one aspect, relates to methods of detecting a nucleotide variation within a nucleic acid of interest comprising (a) a step comprising generating a set of extension products from a first nucleic acid and causing modified nucleotides to be present in the extension products, wherein the modified nucleotides comprise a single type of base; (b) a step comprising hybridizing the extension products to a second nucleic acid; (c) a step comprising contacting the hybridizing nucleic acid with one or more agents that collectively remove the modified nucleotides; (d) a step comprising contacting the hybridizing nucleic acid with a first enzyme that extends the extension products in the presence of three types of nuclease-resistant nucleotides and not in the presence of nucleotides that comprise the same type of base as the modified nucleotides, wherein each of the three types of nuclease-resistant nucleotides comprises a different type of base; (e) a step comprising contacting the hybridizing nucleic acid with a second enzyme that removes nucleotides from the 3' end of the extension products, wherein the second enzyme does not remove the nuclease-resistant nucleotides; (f) a step comprising contacting the hybridizing nucleic acid with a third enzyme that extends the extension products in the presence of nucleotides; (g) a step comprising distinguishing those extension products comprising a nuclease-resistant nucleotide from those extension products not comprising a nuclease-resistant nucleotide, wherein the first nucleic acid is a reference nucleic acid and the second nucleic acid is the nucleic acid of interest or wherein the first nucleic acid is the nucleic acid of interest and the second nucleic acid is a reference nucleic acid, thereby detecting nucleotide variation in the nucleic acid of interest.

The extension products generated from the first nucleic acid can be single or double-stranded. The modified nucleotides can be caused to be present in the extension products by generating the extension products in the presence of modified nucleotides comprising a single type of base, wherein the extension products incorporate the modified nucleotides. The modified nucleotides can be caused to be present in the extension products by modifying nucleotides in the extension products to produce the modified nucleotides. The nucleotides can be modified in the extension products selectively. The nucleotides can be modified in the extension products in a limited way. The nucleotides can be modified in the extension products by chemical modification, enzymatic modification, or a combination.

Additional advantages of the disclosed method and compositions will be set forth in part in the description which follows, and in part will be understood from the description, or may be learned by practice of the disclosed method and compositions. The advantages of the disclosed method and compositions will be realized and attained by means of the elements and combinations particularly pointed out in the appended claims. It is to be understood that both the foregoing general description and the following detailed description are exemplary and explanatory only and are not restrictive of the invention as claimed.

BRIEF DESCRIPTION OF THE DRAWINGS

The accompanying drawings, which are incorporated in and constitute a part of this specification, illustrate several embodiments of the disclosed method and compositions and together with the description, serve to explain the principles of the disclosed method and compositions.

FIG. 4 shows the model oligo triplex.

DETAILED DESCRIPTION

Figure 1:
FIG. 1 shows the extension of a 5' biotinylated PCR products on homoduplex or heteroduplex DNA after site specific removal of uracil. TEER with dNTPs (All), matching nucleotide (U), mismatch nucleotides (A, C, G), on homo and heteroduplex DNA. A mutation in heteroduplex G lane is designated with an arrow (<).

Before the present compounds, compositions, articles, devices, and/or methods are disclosed and described, it is to be understood that they are not limited to specific synthetic methods or specific recombinant biotechnology methods unless otherwise specified, or to particular reagents unless otherwise specified, as such may, of course, vary. It is also to be understood that the terminology used herein is for the purpose of describing particular embodiments only and is not intended to be limiting.

As used in the specification and the appended claims, the singular forms "a," "an" and "the" include plural referents unless the context clearly dictates otherwise. Thus, for example, reference to "a pharmaceutical carrier" includes mixtures of two or more such carriers, and the like.

Ranges can be expressed herein as from "about" one particular value, and/or to "about" another particular value. When such a range is expressed, another embodiment includes from the one particular value and/or to the other particular value. Similarly, when values are expressed as approximations, by use of the antecedent "about," it will be understood that the particular value forms another embodiment. It will be further understood that the endpoints of each of the ranges are significant both in relation to the other endpoint, and independently of the other endpoint. It is also understood that there are a number of values disclosed herein, and that each value is also herein disclosed as "about" that particular value in addition to the value itself. For example, if the value "10" is disclosed, then "about 10" is also disclosed. It is also understood that when a value is disclosed that "less than or equal to" the value, "greater than or equal to the value" and possible ranges between values are also disclosed, as appropriately understood by the skilled artisan. For example, if the value "10" is disclosed the "less than or equal to 10" as well as "greater than or equal to 10" is also disclosed. It is also understood that the throughout the application, data is provided in a number of different formats, and that this data, represents endpoints and starting points, and ranges for any combination of the data points. For example, if a particular data point "10" and a particular data point 15 are disclosed, it is understood that greater than, greater than or equal to, less than, less than or equal to, and equal to 10 and 15 are considered disclosed as well as between 10 and 15.

In this specification and in the claims which follow, reference will be made to a number of terms which shall be defined to have the following meanings:

"Optional" or "optionally" means that the subsequently described event or circumstance may or may not occur, and that the description includes instances where said event or circumstance occurs and instances where it does not.

"Primers" are a subset of probes which are capable of supporting some type of enzymatic manipulation and which can hybridize with a target nucleic acid such that the enzymatic manipulation can occur. A primer can be made from any combination of nucleotides or nucleotide derivatives or analogs available in the art which do not interfere with the enzymatic manipulation.

"Probes" are molecules capable of interacting with a target nucleic acid, typically in a sequence specific manner, for example through hybridization. The hybridization of nucleic acids is well understood in the art and discussed herein. Typically a probe can be made from any combination of nucleotides or nucleotide derivatives or analogs available in the art.

Because of the limitations of sequencing technology, especially sensitivity, numerous scanning technologies for unknown mutations have been developed over the years: denaturing high-performance liquid chromatography (dHPLC) (Xiao W, Oefner P J. Hum Mutat 2001; 17(6):439-74), base excision sequence scanning (BESS), single strand conformation polymorphism (SSCP) (Orita M, et al. *Genomics* 1989; 5(4):874-9), heteroduplex analysis (HA) (Nagamine C M, et al. *Am J Hum Genet.* 1989; 45(2):337-9), conformation sensitive gel electrophoresis (CSGE) (Ganguly A, Prockop D J. *Electrophoresis* 1995; 16(10):1830-5; Ganguly A, et al. *Proc Natl Acad Sci USA* 1993; 90(21):10325-9), denaturing gradient gel electrophoresis (DGGE) (Fodde R, Losekoot M. *Hum Mutat* 1994; 3(2):83-94), constant denaturing gel electrophoresis (CDGE) (Hovig E, et al. *Mutat Res* 1991; 262(1): 63-71), temporal temperature gradient gel electrophoresis (TTGE) (Chen T J, et al. *Clin Chem* 1999; 45(8 Pt 1):1162-7), chemical cleavage of mismatches (Cotton R G, et al. *Proc Natl Acad Sci USA* 1988; 85(12):4397-401, Novack D F, et al. *Proc Natl Acad Sci USA* 1986; 83(3):586-90), enzymatic cleavage of mismatches (Winter E, et al. *Proc Natl Acad Sci USA* 1985; 82(22):7575-9; Myers R M, et al. *Science* 1985; 230(4731):1242-6) and mismatch repair enzymes (Oldenburg M C, et al. *Biotechniques* 2000; 28(2):351-7; Babon J J, et al. *Electrophoresis* 1999; 20(6):1162-70; Youil R, et al. *Genomics* 1996; 32(3):431-5; Brow M A, et al. *J Clin Microbiol* 1996; 34(12):3129-37; Lu A L, Hsu I C. *Genomics* 1992; 14(2):249-55). These technologies have not seen widespread use because they have one or more of the following limitations: laborious, difficult to automate (low-throughput), low sensitivity or difficult to reproduce.

That need in the art is evident by the number of methods being developed to screen for unknown mutations. Single strand conformation polymorphism (SSCP) detects mutations in an unknown sample by comparing its migration rate in a single stranded state to a known sample in a non-denaturing gel, as disclosed by Orita et al., Genomics, 5:874-879 (1989). Changes in nucleotide sequence affect the secondary structure or conformation of a DNA molecule which may alter its migration rate during electrophoresis. This technique, however, is limited to small targets less than 200 bp, has limited sensitivity, and requires rigid electrophoresis conditions to be reproducible. Improvements in SSCP analysis such as dideoxy fingerprinting, both unidirectional (Sarkar et al., Genomics, 13:441-443 (1992)) and bidirectional (Liu et al., Hum. Mol. Genet., 5:107-114 (1996)), and restriction endonuclease fingerprinting (Liu and Sommer, Biotechniques, 18:470-477 (1995)) can detect mutations over a 1 kb span but sacrifice sensitivity for simplicity since the complex pattern of DNA bands generated by these processes makes it difficult to readily detect mutations.

Another method that is used for screening for nucleotide variations in a nucleic acid is based on the differential mobility of heteroduplex molecules as they migrate through a gel matrix. In its simplest form called heteroduplex analysis, an uncharacterized DNA segment, usually an amplification or PCR product, is mixed with the corresponding wild type segment, heated, and allowed to slowly renature, as first described by Nagamine et al. (Am. J. Hum. Genet., 45, 337-339 (1989)). If the uncharacterized nucleic acid has a different sequence than the wild type sequence, heteroduplex molecules are formed. Base mismatches in the heteroduplex alter its migration rate allowing it to be partially resolved from the homoduplex in a non-denaturing gel.

A more sensitive approach called denaturing gradient gel electrophoresis (DGGE) subjects heteroduplex molecules to increasing levels of denaturant in a gradient gel format, as first described by Fisher and Lerman. (Proc. Natl. Acad. Sci. U.S.A., 80:1579-1583 (1983)). As the heteroduplex molecules migrate through the denaturant, they begin to melt, or denature. At this point migration is slowed and is no longer linear. The melting point is slightly different for homoduplex molecules, allowing partial resolution of heteroduplex molecules. Precise control of field strength, temperature and time are critical to achieving reproducible results, and difficult to consistently reproduce.

With constant denaturing gel electrophoresis (CDGE), these variables are less critical since the concentration of denaturant is the same throughout the gel (Hovig et al., Mut. Res., 262:63-71 (1991)). A significant limitation of this technique is that a nucleic acid segment may have more than one melting domain for which separate gels at different denaturant concentrations must be run.

Temporal temperature gradient gel electrophoresis (TTGE) seeks to circumvent this problem by gradually increasing the temperature during electrophoresis, as described by Borresen et al. (Bioradiations, 99:12-113 (1997)). This is a hybrid technique between CDGE and temperature gradient gel electrophoresis which uses temperature only as a denaturant (Rosenbaum and Riesner, Biophys.

Chem., 26:235-246 (1987)). As expected, however, this technique is also difficult to perform and also difficult to reproduce.

A recently introduced technique called base excision sequence scanning (BESS) improves upon dideoxy fingerprinting with ddTTP by obviating the need for a separate sequencing reaction (Epicentre Technologies, Madison, Wis.). The target of interest is amplified by PCR using a labeled primer and a limiting amount of dUTP. After amplification, the products are treated with uracil DNA glycosylase to cleave at uracil sites. Denaturing gel electrophoresis of the fragments then produces a ladder almost identical to a dideoxy T sequencing ladder. The technique is useful for screening DNA segments up to 1 kb for mutations, but is limited by the resolution of gel electrophoresis and it does not detect G to C transversions or vice versa.

Another recently introduced technique uses a structure specific endonuclease called cleavase to digest intrastrand structures and produce fragment length polymorphisms (CFLP) and is described by Brow et al., J. Clin. Microbiol., 34:3129-3137 (1996). The structures are created by denaturing a segment of DNA and then quickly cooling it to the digestion temperature and adding the enzyme. The folding pattern for a given segment may be altered by sequence variations that upon digestion with the enzyme produces a unique banding pattern on a denaturing gel. This technique, however, is severely limited by the resolution of the gel electrophoresis and the complex pattern of DNA bands generated by the process which makes it difficult to detect mutations.

Detection of mutations by chemical or enzymatic cleavage of base pair mismatches in heteroduplex DNA has been described by Noack et al., Proc. Natl. Acad. Sci. U.S.A., 83:586-590 (1986), Cotton et al. Proc. Natl. Acad. Sci. U.S.A., 85:4394-4401 (1988), Cotton et al., U.S. Pat. No. 5,202,231, (Winter et al., Proc. Natl. Acad. Sci. U.S.A., 82:7575-7579 (1989), Myers et al., Science, 230:1245-1246 (1985)), (Lu and Hsu, Genomics, 14:249-255 (1992)), and U.S. Pat. No. 5,698,400. Many of these techniques are limited by the inability of the cleavage reagents to recognize all types of base pair mismatches, and for others this can be overcome by analyzing both strands of a DNA segment. To date, widespread use of these techniques has not been observed, partly because they require highly toxic reagents and the procedures are difficult to perform.

The miniaturization of the DNA hybridization process onto a small solid surface, known as a DNA chip or micro array, allows the analysis of DNA segments without gel electrophoresis. See Macevicz, U.S. Pat. No. 5,002,867, Drmanac., U.S. Pat. No. 5,202,231, Lipshutz et al., Biotechniques, 9(3):442-447 (1995) and Chee et al., Science, 274: 610-614 (1996). The resolution of gel electrophoresis, however, strictly limits the size of the DNA segment that can be analyzed for all of the aforementioned mutation detection technologies including DNA sequencing and the high cost of the equipment and chips used in this process limit its wide spread use.

Recently a technique called endo V mutation scanning has been introduced and improved for detecting unknown mutations (Pincas H, et al. *Nucl. Acid Res* 2004; 32(19):e148). In its improved format, it is capable of detecting unknown mutations present at a ratio 1:50 and 1:100 (mutant:wildtype) for p53 and K-ras genes respectively. Although an improvement over existing technology, it is dependent on gel electrophoresis for detection and is difficult to interpret.

The disclosed methods and compositions provide needed improvements over these other methods by providing methods which can detect all possible base variations including single and multiple base substitutions, insertions and deletions. These variations may occur at one or more sites and affect one or more nucleotides at each site for a given locus. Secondly, as a screening process, these methods provide a clear positive or negative result. Thirdly, the process is not limited by the resolution power of gel electrophoresis and therefore allow the analysis of DNA segments greater that 1 kb in size. Lastly, by way of eliminating electrophoretic detection, it is highly amenable to automation and therefore suitable for high volume screening.

Disclosed herein are methods of detecting nucleotide variations in a nucleic acid. It is understood and herein contemplated that the methods disclosed herein allow for rapid and sensitive detection of rare mutations including but not limited to mutations comprising single nucleotide variations in the presence of excess normal DNA. Thus, for example, disclosed herein are methods of detecting a nucleotide variation within a nucleic acid of interest comprising (a) a step comprising generating a set of extension products from a first nucleic acid and causing modified nucleotides to be present in the extension products, wherein the modified nucleotides comprise a single type of base, (b) a step comprising hybridizing the extension products to a second nucleic acid, (c) a step comprising contacting the hybridizing nucleic acid with one or more agents that collectively remove the modified nucleotides, (d) a step comprising contacting the hybridizing nucleic acid with a first enzyme that extends the extension products in the presence of three types of nuclease-resistant nucleotides and not in the presence of nucleotides that comprise the same type of base as the modified nucleotides, wherein each of the three types of nuclease-resistant nucleotides comprises a different type of base, (e) a step comprising contacting the hybridizing nucleic acid with a second enzyme that removes nucleotides from the 3' end of the extension products, wherein the second enzyme does not remove the nuclease-resistant nucleotides, (f) a step comprising contacting the hybridizing nucleic acid with a third enzyme that extends the extension products in the presence of nucleotides, (g) a step comprising distinguishing those extension products comprising a nuclease-resistant nucleotide from those extension products not comprising a nuclease-resistant nucleotide, wherein the first nucleic acid is a reference nucleic acid and the second nucleic acid is the nucleic acid of interest or wherein the first nucleic acid is the nucleic acid of interest and the second nucleic acid is a reference nucleic acid, thereby detecting nucleotide variation in the nucleic acid of interest. The extension products generated from the first nucleic acid can be single or double-stranded.

The modified nucleotides can be caused to be present in the extension products by, for example, generating the extension products in the presence of modified nucleotides comprising a single type of base, wherein the extension products incorporate the modified nucleotides. Particularly useful forms of the method produce, on average, one or a few modified nucleotides in an extension product strand. The modified nucleotides can be incorporated generally at random such that collectively the set of extension products have modified nucleotides at many, most or all of the positions where the modified nucleotide could be incorporated. This allows assessment of many, most or all of the relevant nucleotide positions in the nucleic acid of interest. The modified nucleotides can be caused to be present in the extension products by, for example, modifying nucleotides in the extension products to produce the modified nucleotides. For example, the nucleotides can be modified in the extension products by chemical modification, enzymatic modification, or a combination. An example of this is described in Example 3. Numerous chemical agents are known that can modified nucleotides. Similarly, enzymes are known that can modify nucleotides. Useful modifications allow and/or target the modified nucleotides for removal from the extended strands.

Modification of nucleotides in the extension products can be done selectively. By selectively is meant that only certain types of nucleotides and/or certain types of bases are modified or targeted for modification. Most useful is modification where a single type of base is modified and/or targeted for modification. Modification of nucleotides in the extension products can also be done in a limited way. By modification in a limited way is meant that only some of the nucleotides are modified. For example, where modification is done selectively on, for example, nucleotides comprising a single type of base, modification in a limited way means that only some of the nucleotides comprising the selected type of base are modified. Modification in a limited way is thus a limited reaction or operation. Typically, modification in a limited way is accomplished by performing a modification reaction or exposing the extension product to modifying conditions for a limited time or under limiting conditions such that only some of the nucleotides that could be modified are modified. Particularly useful forms of modification in a limited way produce, on average, one or a few modified nucleotides in an extension product strand. The nucleotides can be modified generally at random such that collectively the set of extension products have modified nucleotides at many, most or all of the positions where nucleotides could be modified. This allows assessment of many, most or all of the relevant nucleotide positions in the nucleic acid of interest.

The methods for detection of nucleic acid variation disclosed herein have many uses including but not limited to the detection or diagnosis of the presence of a disease or condition such as cancer, assessing the susceptibility or risk for a disease or condition associated with a nucleic acid variation, the monitoring disease progression, and the determination of susceptibility or resistance to therapeutic treatment. Thus for example, disclosed herein are methods for detecting the presence of a cancer comprising detecting a nucleotide variation within a nucleic acid of interest comprising (a) a step comprising generating a set of extension products from a first nucleic acid and causing modified nucleotides to be present in the extension products, wherein the modified nucleotides comprise a single type of base, (b) a step comprising hybridizing the extension products to a second nucleic acid, (c) a step comprising contacting the hybridizing nucleic acid with one or more agents that collectively remove the modified nucleotides, (d) a step comprising contacting the hybridizing nucleic acid with a first enzyme that extends the extension products in the presence of three types of nuclease-resistant nucleotides and not in the presence of nucleotides that comprise the same type of base as the modified nucleotides, wherein each of the three types of nuclease-resistant nucleotides comprises a different type of base, (e) a step comprising contacting the hybridizing nucleic acid with a second enzyme that removes nucleotides from the 3' end of the extension products, wherein the second enzyme does not remove the nuclease-resistant nucleotides, (f) a step comprising contacting the hybridizing nucleic acid with a third enzyme that extends the extension products in the presence of nucleotides, (g) a step comprising distinguishing those extension products comprising a nuclease-resistant nucleotide from those extension products not comprising a nuclease-resistant nucleotide, wherein the first nucleic acid is a reference nucleic acid and the second nucleic acid is the nucleic acid of interest or wherein the first nucleic acid is the nucleic acid of interest and the second nucleic acid is a reference nucleic acid, thereby detecting nucleotide variation in the nucleic acid of interest, wherein the presence of variation in the nucleic acid of interest relative to the reference nucleic acid indicates the presence of a cancer. The extension products generated from the first nucleic acid can be single or double-stranded. The modified nucleotides can be caused to be present in the extension products by generating the extension products in the presence of modified nucleotides comprising a single type of base, wherein the extension products incorporate the modified nucleotides. The modified nucleotides can be caused to be present in the extension products by modifying nucleotides in the extension products to produce the modified nucleotides. The nucleotides can be modified in the extension products selectively. The nucleotides can be modified in the extension products in a limited way. The nucleotides can be modified in the extension products by chemical modification, enzymatic modification, or a combination.

The disclosed methods can create a situation where there are substantially no extension products not comprising a nuclease-resistant nucleotide. Thus, the step of distinguishing extension products comprising a nuclease resistant nucleotide from those extension products not comprising a nuclease-resistant nucleotide can be accomplished, for example, by merely detecting the presence of extension products. For example, a sample wherein a nuclease-resistant nucleotide is not incorporated into an extension product extended in the presence of nuclease-resistant nucleotides results in the extension product being digested upon exposure to an enzyme (e.g., an exonuclease such as Exonuclease III). Conversely, a sample wherein a nuclease-resistant nucleotide is incorporated into an extension product extended in the presence of nuclease-resistant nucleotides results in the extension product being resistant to digestion by an enzyme (e.g., an exonuclease). It is understood that the second enzyme can comprise any enzyme known in the art that can remove nucleotides in a 3' to 5' direction (i.e., from the 3' end). Thus, for example, the enzyme can be an exonuclease such as Exonuclease III. Other enzymes contemplated herein to be utilized as the second enzyme include but are not limited to Trex I, Trex II, T7, and Exonuclease T. Thus, disclosed herein are methods wherein the second enzyme can be an exonuclease. Also disclosed are methods wherein the second enzyme is exonuclease III. It is also understood that in methods wherein the enzyme is an exonuclease that digests 3' to 5', any nucleotides 5' of the nuclease resistant nucleotide in the extension products are protected from removal by the enzyme. Similarly, extension products in which no nuclease-resistant nucleotide is present can be digested by the enzyme. Thus, disclosed herein are methods wherein there are substantially no extension products not comprising a nuclease-resistant nucleotide following use of the enzyme that removes nucleotides from the 3' end of the extension products, wherein distinguishing those extension products comprising a nuclease-resistant nucleotide from those extension products not comprising a nuclease-resistant nucleotide comprises detecting the presence of extension products.

The methods disclosed herein contemplate situations wherein extension products are only present following nuclease digestion if a nuclease-resistant nucleotide was incorporated into an extension product. A "nuclease-resistant nucleotide" refers to any nucleotide that is resistant to a given nuclease. It is understood and herein contemplated that such "nuclease-resistant nucleotides" can be naturally occurring or synthesized. It is understood that there are many such nucleotides known to those of skill in the art and the use of any one nuclease-resistant nucleotide will depend on the nuclease being used. Examples of nuclease-resistant nucleotides include but are not limited to thio-modified deoxynucleotides and borano-modified nucleotides. Thus, for example disclosed are methods wherein the nuclease-resistant nucleotides comprise α-thio-deoxynucleotides. Disclosed herein are methods of detecting nucleic acid variation, wherein a nuclease-resistant nucleotide is incorporated into an extension product in the presence of nuclease-resistant nucleotides only if a nucleotide variation was present in the nucleic acid of interest. Also disclosed are methods, wherein a nuclease-resistant nucleotide is incorporated into an extension product in the presence of nuclease-resistant nucleotides substantially only if a nucleotide variation was present in the nucleic acid of interest.

The disclosed methods contemplate that as a result of performing the steps disclosed herein that the modified nucleotides of the disclosed methods will incorporate into the nucleic acid produced from (templated by) a first nucleic acid (which can be a nucleic acid of interest or a reference nucleic acid). It is further contemplated that the site(s) where nucleotide variation occurs will be revealed by incorporation of a modified nucleotide at the position(s) corresponding to the site(s) where nucleotide variation occurs. Thus, disclosed herein are methods wherein the nucleotide variation was present in the nucleic acid of interest at a site corresponding to the location of a modified nucleotide in the extension products. It is understood and herein contemplated that any number of modified nucleotides known to those of skill in the art can be used in the disclosed methods. Those of skill in the art will know how to determine the appropriateness of a given modified nucleotide. As used in the methods disclosed herein, modified nucleotides include but are not limited to 7, 8-dihydro-8-oxoguanine (8-oxoguanine), 8-oxoadenine, fapy-guanine, methyl-fapy-guanine, fapy-adenine, aflatoxin $B_1$-fapy-guanine, 5-hydroxy-cytosine, 5-hydroxy-uracil, and ring-opened N-7 guanine adducts (7-methylguanine). Generally, modified nucleotides can be chosen as nucleotides that can be selectively removed from a nucleic acid strand by one or more agents. Useful agents for removal of modified nucleotides or repair of DNA include, for example, uracil DNA glycosylase, APE I (human apurinic/apyrimidinic endonuclease), FPG (formamidopyrimidine-DNA glycosylase a.k.a 8-oxyguanine DNA glycosylase), Endonuclease IV and kinase, Endo III, Endo VIII, hOGG1, T7 Endo I, T4 PDG and afu UDG. Modified nucleotides can also be removed via, for example, base specific cleavage by random incorporation of an alpha-thionucleotide or ribose nucleotide during PCR followed by chemical cleavage.

Selective removal allows selective replacement of substantially only modified nucleotides. This allows the disclosed methods to operate so as to identify the type of nucleotide that is variant in the nucleic acid stand of interest. By selective removal is meant that substantially only the nucleotides targeted or intended to be removed are removed by the action of the agents. It is not required that all, most or even many of the modified nucleotides be removed to constitute selective removal. Rather, it is the absence of removal of nucleotides not targeted or intended to be removed that constitutes selective removal. Generally, the nature and type of modified nucleotide and the nature and type of agents will establish which nucleotides are removed.

The disclosed methods of detecting nucleotide variation can utilize agents to remove modified nucleotides. It is contemplated herein that the agents can remove the modified nucleotides through the actions of a single agent or through the actions of multiple agents. Thus, one agent my create conditions by which another agent my function. For example, one agent may remove the base of the modified nucleotide providing a site for the action of an endonuclease that cleaves only at abasic nucleotides. Thus, disclosed herein are methods wherein the one or more of the agents removes the base from the modified nucleotides. There are many agents known in the art that may be used alone or in combination in the disclosed methods. Those of skill in the art are aware of agents that may be used in the disclosed methods. It is understood and contemplated herein that the agents can comprise enzymes such as nucleases and glycosylases. Thus, disclosed herein are methods wherein the agents comprise an endonuclease. Also disclosed are methods wherein the one or more agents comprise Endonuclease IV. Also disclosed are methods wherein the one or more agents comprise formamidopyrimidine-DNA glycosylase (FPG).

In the methods disclosed herein, removal of the modified nucleotides and extension of the extension product in the presence of nuclease-resistant nucleotides can be performed sequentially or simultaneously.

The methods disclosed herein contemplate the use of an enzyme to remove and replace the modified nucleotide and replace it with a labeled nucleotide. One example of an enzyme capable of replacing the modified nucleotide with a labeled nucleotide is a polymerase. Thus disclosed herein are methods wherein the first enzyme comprises a polymerase. It is understood that in one aspect, the polymerase can be a DNA polymerase. It is also understood and herein disclosed that the polymerase can be thermostable. Thus, disclosed are methods wherein the first enzyme is a thermostable polymerase. It is understood and herein contemplated that any number of thermostable polymerases can be used in the disclosed methods. Thus, for example, the third enzyme can comprise THERMOSEQUENASE.

It is understood and contemplated herein that there are numerous ways known to those of skill in the art to distinguish extension products comprising a nuclease-resistant nucleotide from those extension products not comprising nuclease resistant extension products. As noted above one such way is through the mere presence or absence of an extension product. This can be the case, for example, where only those extension products comprising a nuclease-resistant nucleotide are present and where only those extension products comprising nucleotide variations incorporated a nuclease-resistant nucleotide. Nuclease-resistant nucleotides can represent the presence of nucleotide variations because in the method nuclease-resistant nucleotides can replace modified nucleotides in extension products when the replaced modified nucleotide corresponds to the position of the variation.

The extension products can also be distinguished via PCR. Real time PCR (rtPCR) is particularly useful for this. Any form of PCR or real time PCR can be used with the disclosed methods. A variety of PCR forms and protocols are known and can be used. For example, PCR can be mediated by two or more primers, where one or more of the primers comprise a fluorescent label. For example, the primer can comprise a fluorescent change primer. The primers can be designed to hybridize to particular sequences present in the extension products and/or hybridizing nucleic acids. Thus, contemplated herein are methods wherein the first nucleic acid comprises a primer sequence, wherein at least some of the extension products in which a nuclease-resistant nucleotide is present are extended at least to the primer sequence in the first nucleic acid. That is, the extension products can be extended such that sequence complementary to the primer sequence in the first nucleic acid is present. The complement to the primer sequence can then be used as a primer binding site for primer used for amplification or replication of the extension products.

Other forms of nucleic acid amplification and signal amplification can also be used. Generally, the goal of PCR or other amplification method is to create and/or increase the signal from the extension products to be detected. In some forms of the disclosed methods, differential amplifiability (or detectability) of extension products that have or do not have labeled or nuclease-resistant nucleotides incorporated provide the basis for distinguishing between these extension products.

Another method of distinguishing extension products is through the use of labeled nucleotides. For example, disclosed herein are methods wherein the nuclease-resistant nucleotide is also labeled. Thus, for example, disclosed herein are methods wherein extension of the extension products incorporates one or more labeled nuclease-resistant nucleotides into the extension products. As another example, modified nucleotides that are removed form extension products can be replaced with labeled nucleotides.

Also disclosed are methods wherein the extension products are labeled with a detectable label and the extension products are distinguished by performing gel electrophoresis of the extended extension products, wherein the electrophoresis is of sufficient resolution to distinguish between a labeled extension product that is not further extended and a full length nucleic acid.

It is understood and herein contemplated that there are occasions where each type of base needs to be accounted for to determine the presence of a nucleotide variation or distinguish between possible variants. Also disclosed herein are methods of detecting nucleotide variation further comprising performing the steps of the method one or more additional times each time using a different type of modified nucleotide comprising a different type of base. Also disclosed are methods wherein the steps of the method are performed at least once using each of four different modified nucleotides, wherein each of the four different modified nucleotides comprises a different one of the four types of base. This allows, for example, each type of base to be assessed or accounted for in the nucleic acid of interest. This can allow, for example, an assessment or determination of nucleotide variation at any position and of any identity in the nucleic acid of interest.

The methods disclosed herein also can be used in conjunction with DNA sequencing techniques to identify the location of the nucleotide variation. Thus disclosed herein are methods of detection nucleotide variation further comprising sequencing the extension products with a nucleotide variation and comparing that sequence to a reference sequence, thereby specifically identifying the nucleotide variation in the first nucleic acid.

The methods disclosed herein can be used to detect nucleotide variation wherein the nucleotide variation is a single nucleotide variation. Moreover, the disclosed methods can detect nucleotide variation, wherein the nucleotide variation detected is a nucleotide variation in a single nucleotide.

Also disclosed herein are methods of detecting a nucleotide variation within a first nucleic acid comprising:

(a) a step comprising generating a set of extension products from a reference nucleic acid and causing modified nucleotides to be present in the extension products, wherein the modified nucleotides comprise a single type of base;

(b) a step comprising hybridizing the extension products to the first nucleic acid;

(c) a step comprising contacting the hybridizing nucleic acid with one or more agents that collectively remove the modified nucleotides;

(d) a step comprising contacting the hybridizing nucleic acid with a first enzyme that extends the extension products in the presence of three types of labeled nucleotides and not in the presence of nucleotides that comprise the same type of base as the modified nucleotides, wherein each of the three types of labeled nucleotides comprises a different type of base; and (e) a step comprising distinguishing those extension products comprising a labeled nucleotide from those extension products not comprising a labeled nucleotide, thereby detecting nucleotide variation in the first nucleic acid. The extension products generated from the first nucleic acid can be single or double-stranded. The modified nucleotides can be caused to be present in the extension products by generating the extension products in the presence of modified nucleotides comprising a single type of base, wherein the extension products incorporate the modified nucleotides. The modified nucleotides can be caused to be present in the extension products by modifying nucleotides in the extension products to produce the modified nucleotides. The nucleotides can be modified in the extension products selectively. The nucleotides can be modified in the extension products in a limited way. The nucleotides can be modified in the extension products by chemical modification, enzymatic modification, or a combination.

The disclosed methods make use of enzymes. In the context of the methods, these enzymes perform certain functions and any enzymes that can perform the required function can be used. Generally, the functions are well known reactions involving nucleic acids and nucleotides. Many suitable enzymes are know and can be used to catalyze the required reactions, and the mode and manner of use of such enzymes for such reactions is well known. Several parts of the disclosed methods require extension of nucleic acids. Any nucleic acid polymerase that can extend a strand can be used. Useful polymerases can extend nucleic acids and replicate nucleic acids based on a template nucleic acid. Other steps in the methods require removal of nucleotides. General nucleotide removal can be accomplished using any suitable nuclease. Exonucleases are particularly useful in the disclosed methods. In some steps of the disclosed methods, removal of modified nucleotides is required. Enzymes and/or chemical agents can be used to accomplish this as described more fully elsewhere herein. Particularly useful are selective endonucleases and nucleotide glycosylases.

A. Nucleic Acids

The disclosed method and compositions make use of various nucleic acids. Generally, any nucleic acid can be used in the disclosed method. For example, the disclosed nucleic acids of interest and the disclosed reference nucleic acids can be chosen based on the desired analysis and information that is to be obtained or assessed. The disclosed methods also produce new and altered nucleic acids. The nature and structure of such nucleic acids will be established by the manner in which they are produced and manipulated in the methods. Thus, for example, extension products and hybridizing nucleic acids are produced in the disclosed methods. As used herein, hybridizing nucleic acids are hybrids of extension products and the second nucleic acid.

It is understood and contemplated herein that a nucleic acid of interest can be any nucleic acid to which the determination of the presence or absence of nucleotide variation is desired.

Thus, for example, the nucleic acid of interest can comprise a sequence that corresponds to the wild-type sequence of the reference nucleic acid. It is further disclosed herein that the disclosed methods can be performed where the first nucleic acid is a reference nucleic acid and the second nucleic acid is a nucleic acid of interest or where the first nucleic acid is the nucleic acid of interest and the second nucleic acid is the reference nucleic acid.

It is understood and herein contemplated that a reference nucleic acid can be any nucleic acid against which a nucleic acid of interest is to be compared. Typically, the reference nucleic acid has a known sequence (and/or is known to have a sequence of interest as a reference). Although not required, it is useful if the reference sequence has a known or suspected close relationship to the nucleic acid of interest. For example, if a single nucleotide variation is desired to be detected, the reference sequence can be usefully chosen to be a sequence that is a homolog or close match to the nucleic acid of interest, such as a nucleic acid derived from the same gene or genetic element from the same or a related organism or individual. Thus, for example, it is contemplated herein that the reference nucleic acid can comprise a wildtype sequence or alternatively can comprise a known mutation including, for example, a mutation the presence or absence of which is associated with a disease or resistance to therapeutic treatment. Thus, for example, it is contemplated that the disclosed methods can be used to detect or diagnose the presence of known mutations in a nucleic acid of interest by comparing the nucleic acid of interest to a reference nucleic acid that comprises a wildtype sequence (i.e., is known not to possess the mutation) and examining for the presence or absence of variation in the nucleic acid of interest, where the absence of variation would indicate the absence of a mutation. Alternatively, the reference nucleic acid can possess a known mutation. Thus, for example, it is contemplated that the disclosed methods can be used to detect susceptibility for a disease or condition by comparing the nucleic acid of interest to a reference nucleic acid comprising a known mutation that indicates susceptibility for a disease and examining for the presence or absence of the mutation, wherein the presence of the mutation indicates a disease.

Herein, the term "nucleotide variation" refers to any change or difference in the nucleotide sequence of a nucleic acid of interest relative to the nucleotide sequence of a reference nucleic acid. Thus, a nucleotide variation is said to occur when the sequences between the reference nucleic acid and the nucleic acid of interest (or its complement, as appropriate in context) differ. Thus, for example, a substitution of an adenine (A) to a guanine (G) at a particular position in a nucleic acid would be a nucleotide variation provided the reference nucleic acid comprised an A at the corresponding position. It is understood and herein contemplated that the determination of a variation is based upon the reference nucleic acid and does not indicate whether or not a sequence is wildtype. Thus, for example, when a nucleic acid with a known mutation is used as the reference nucleic acid, a nucleic acid not possessing the mutation (including a wild-type nucleic acid) would be considered to possess a nucleotide variation (relative to the reference nucleic acid).

B. Nucleotides

The disclosed methods and compositions make use of various nucleotides. Throughout this application and the methods disclosed herein reference is made to the type of base for a nucleotide. It is understood and contemplated herein that where reference is made to a type of base, this refers a base that in a nucleotide in a nucleic acid strand is capable of hybridizing (binding) to a defined set of one or more of the canonical bases. Thus, for example, where reference is made to extension products extended in the presence of three types of nuclease resistant nucleotides and not in the presence of nucleotides that comprise the same type of base as the modified nucleotides, this means that if, for example, the base of the modified nucleotide was an adenine (A), the nuclease-resistant nucleotides can be, for example, guanine (G), thymine (T), and cytosine (C). Each of these bases (which represent the four canonical bases) is capable of hybridizing to a different one of the four canonical bases and thus each qualify as a different type of base as defined herein. As another example, inosine base pairs primarily with adenine and cytosine (in DNA) and thus can be considered a different type of base from adenine and from cytosine—which base pair with thymine and guanine, respectively—but not a different type of base from guanine or thymine—which base pair with cytosine and adenine, respectively—because the base pairing of guanine and thymine overlaps (that is, is not different from) the hybridization pattern of inosine Any type of modified or alternative base can be used in the disclosed methods and compositions, generally limited only by the capabilities of the enzymes used to use such bases. Many modified and alternative nucleotides and bases are known, some of which are described below and elsewhere herein. The type of base that such modified and alternative bases represent can be determined by the pattern of base pairing for that base as described herein. Thus for example, if the modified nucleotide was adenine, any analog, derivative, modified, or variant base that based pairs primarily with thymine would be considered the same type of base as adenine. In other words, so long as the analog, derivative, modified, or variant has the same pattern of base pairing as another base, it can be considered the same type of base. Modifications can made to the sugar or phosphate groups of a nucleotide. Generally such modifications will not change the base pairing pattern of the base. However, the base pairing pattern of a nucleotide in a nucleic acid strand determines the type of base of the base in the nucleotide.

Modified nucleotides to be incorporated into extension products and to be selectively removed by the disclosed agents in the disclosed methods can be any modified nucleotide that functions as needed in the disclosed method as is described elsewhere herein. Modified nucleotides can also be produced in existing nucleic acid strands, such as extension products, by, for example, chemical modification, enzymatic modification, or a combination.

Many types of nuclease-resistant nucleotides are known and can be used in the disclosed methods. For example, nucleotides have modified phosphate groups and/or modified sugar groups can be resistant to one or more nucleases. Nuclease-resistance is defined herein as resistance to removal from a nucleic acid by any one or more nucleases. Generally, nuclease resistance of a particular nucleotide can be defined in terms of a relevant nuclease. Thus, for example, if a particular nuclease is used in the disclosed method, the nuclease-resistant nucleotides need only be resistant to that particular nuclease. Examples of useful nuclease-resistant nucleotides include thio-modified nucleotides and borano-modified nucleotides.

There are a variety of molecules disclosed herein that are nucleic acid based. Non-limiting examples of these and other molecules are discussed herein. It is understood that for example, a nucleotide is a molecule that contains a base moiety, a sugar moiety and a phosphate moiety. Nucleotides can be linked together through their phosphate moieties and sugar moieties creating an internucleoside linkage. The base moiety of a nucleotide can be adenin-9-yl (adenine, A), cytosin-1-yl (cytosine, C), guanin-9-yl (guanine, G), uracil-1-yl (uracil, U), and thymin-1-yl (thymine, T). The sugar moiety of a nucleotide is a ribose or a deoxyribose. The phosphate moiety of a nucleotide is pentavalent phosphate. A non-limiting example of a nucleotide would be 3'-AMP (3'-adenosine monophosphate) or 5'-GMP (5'-guanosine monophosphate).

A nucleotide analog is a nucleotide which contains some type of modification to either the base, sugar, or phosphate moieties. Modifications to the base moiety would include natural and synthetic modifications of A, C, G, and T/U as well as different purine or pyrimidine bases, such as uracil-5-yl (ψ), hypoxanthin-9-yl (inosine, I), and 2-aminoadenin-9-yl. A modified base includes but is not limited to 5-methylcytosine (5-me-C), 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl uracil and cytosine, 6-azo uracil, cytosine and thymine, 5-uracil (pseudouracil), 4-thiouracil, 8-halo, 8-amino, 8-thiol, 8-thioalkyl, 8-hydroxyl and other 8-substituted adenines and guanines, 5-halo particularly 5-bromo, 5-trifluoromethyl and other 5-substituted uracils and cytosines, 7-methylguanine and 7-methyladenine, 8-azaguanine and 8-azaadenine, 7-deazaguanine and 7-deazaadenine and 3-deazaguanine and 3-deazaadenine. Additional base modifications can be found for example in U.S. Pat. No. 3,687,808, Englisch et al., Angewandte Chemie, International Edition, 1991, 30, 613, and Sanghvi, Y. S., Chapter 15, Antisense Research and Applications, pages 289-302, Crooke, S. T. and Lebleu, B. ed., CRC Press, 1993. Certain nucleotide analogs, such as 5-substituted pyrimidines, 6-azapyrimidines and N-2, N-6 and O-6 substituted purines, including 2-aminopropyladenine, 5-propynyluracil and 5-propynylcytosine. 5-methyl-cytosine can increase the stability of duplex formation. Often time base modifications can be combined with for example a sugar modification, such as 2'-O-methoxyethyl, to achieve unique properties such as increased duplex stability. There are numerous U.S. patents such as U.S. Pat. Nos. 4,845,205; 5,130,302; 5,134,066; 5,175,273; 5,367,066; 5,432,272; 5,457,187; 5,459,255; 5,484,908; 5,502,177; 5,525,711; 5,552,540; 5,587,469; 5,594,121, 5,596,091; 5,614,617; and 5,681,941, which detail and describe a range of base modifications. Each of these patents is herein incorporated by reference.

Nucleotide analogs can also include modifications of the sugar moiety. Modifications to the sugar moiety would include natural modifications of the ribose and deoxy ribose as well as synthetic modifications. Sugar modifications include but are not limited to the following modifications at the 2' position: OH; F; O-, S-, or N-alkyl; O-, S-, or N-alkenyl; O-, S- or N-alkynyl; or O-alkyl-O-alkyl, wherein the alkyl, alkenyl and alkynyl may be substituted or unsubstituted C1 to C10, alkyl or C2 to C10 alkenyl and alkynyl. 2' sugar modifications also include but are not limited to —O[(CH2)n O]m CH3, —O(CH2)n OCH3, —O(CH2)n NH2, —O(CH2)n CH3, —O(CH2)n —ONH2, and —O(CH2)n ON[(CH2)n CH3)]2, where n and m are from 1 to about 10.

Other modifications at the 2' position include but are not limited to: C1 to C10 lower alkyl, substituted lower alkyl, alkaryl, aralkyl, O-alkaryl or O-aralkyl, SH, SCH3, OCN, Cl, Br, CN, CF3, OCF3, SOCH3, SO2 CH3, ONO2, NO2, N3, NH2, heterocycloalkyl, heterocycloalkaryl, aminoalkylamino, polyalkylamino, substituted silyl, an RNA cleaving group, a reporter group, an intercalator, a group for improving the pharmacokinetic properties of an oligonucleotide, or a group for improving the pharmacodynamic properties of an oligonucleotide, and other substituents having similar properties. Similar modifications may also be made at other positions on the sugar, particularly the 3' position of the sugar on the 3' terminal nucleotide or in 2'-5' linked oligonucleotides and the 5' position of 5' terminal nucleotide. Modified sugars would also include those that contain modifications at the bridging ring oxygen, such as CH2 and S. Nucleotide sugar analogs may also have sugar mimetics such as cyclobutyl moieties in place of the pentofuranosyl sugar. There are numerous U.S. patents that teach the preparation of such modified sugar structures such as U.S. Pat. Nos. 4,981,957; 5,118,800; 5,319,080; 5,359,044; 5,393,878; 5,446,137; 5,466,786; 5,514,785; 5,519,134; 5,567,811; 5,576,427; 5,591,722; 5,597,909; 5,610,300; 5,627,053; 5,639,873; 5,646,265; 5,658,873; 5,670,633; and 5,700,920, each of which is herein incorporated by reference in its entirety.

Nucleotide analogs can also be modified at the phosphate moiety. Modified phosphate moieties include but are not limited to those that can be modified so that the linkage between two nucleotides contains a phosphorothioate, chiral phosphorothioate, phosphorodithioate, phosphotriester, aminoalkylphosphotriester, methyl and other alkyl phosphonates including 3'-alkylene phosphonate and chiral phosphonates, phosphinates, phosphoramidates including 3'-amino phosphoramidate and aminoalkylphosphoramidates, thionophosphoramidates, thionoalkylphosphonates, thionoalkylphosphotriesters, and boranophosphates. It is understood that these phosphate or modified phosphate linkage between two nucleotides can be through a 3'-5' linkage or a 2'-5' linkage, and the linkage can contain inverted polarity such as 3'-5' to 5'-3' or 2'-5' to 5'-2'. Various salts, mixed salts and free acid forms are also included. Numerous U.S. patents teach how to make and use nucleotides containing modified phosphates and include but are not limited to, U.S. Pat. Nos. 3,687,808; 4,469,863; 4,476,301; 5,023,243; 5,177,196; 5,188,897; 5,264,423; 5,276,019; 5,278,302; 5,286,717; 5,321,131; 5,399,676; 5,405,939; 5,453,496; 5,455,233; 5,466,677; 5,476,925; 5,519,126; 5,536,821; 5,541,306; 5,550,111; 5,563,253; 5,571,799; 5,587,361; and 5,625,050, each of which is herein incorporated by reference.

It is understood that nucleotide analogs need only contain a single modification, but may also contain multiple modifications within one of the moieties or between different moieties.

Nucleotide substitutes are molecules having similar functional properties to nucleotides, but which do not contain a phosphate moiety, such as peptide nucleic acid (PNA). Nucleotide substitutes are molecules that will recognize nucleic acids in a Watson-Crick or Hoogsteen manner, but which are linked together through a moiety other than a phosphate moiety. Nucleotide substitutes are able to conform to a double helix type structure when interacting with the appropriate target nucleic acid.

Nucleotide substitutes are nucleotides or nucleotide analogs that have had the phosphate moiety and/or sugar moieties replaced. Nucleotide substitutes do not contain a standard phosphorus atom. Substitutes for the phosphate can be for example, short chain alkyl or cycloalkyl internucleoside linkages, mixed heteroatom and alkyl or cycloalkyl internucleoside linkages, or one or more short chain heteroatomic or heterocyclic internucleoside linkages. These include those having morpholino linkages (formed in part from the sugar portion of a nucleoside); siloxane backbones; sulfide, sulfoxide and sulfone backbones; formacetyl and thioformacetyl backbones; methylene formacetyl and thioformacetyl backbones; alkene containing backbones; sulfamate backbones;

methyleneimino and methylenehydrazino backbones; sulfonate and sulfonamide backbones; amide backbones; and others having mixed N, O, S and CH2 component parts. Numerous U.S. patents disclose how to make and use these types of phosphate replacements and include but are not limited to U.S. Pat. Nos. 5,034,506; 5,166,315; 5,185,444; 5,214,134; 5,216,141; 5,235,033; 5,264,562; 5,264,564; 5,405,938; 5,434,257; 5,466,677; 5,470,967; 5,489,677; 5,541,307; 5,561,225; 5,596,086; 5,602,240; 5,610,289; 5,602,240; 5,608,046; 5,610,289; 5,618,704; 5,623,070; 5,663,312; 5,633,360; 5,677,437; and 5,677,439, each of which is herein incorporated by reference.

It is also understood in a nucleotide substitute that both the sugar and the phosphate moieties of the nucleotide can be replaced, by for example an amide type linkage (aminoethylglycine) (PNA). U.S. Pat. Nos. 5,539,082; 5,714,331; and 5,719,262 teach how to make and use PNA molecules, each of which is herein incorporated by reference. (See also Nielsen et al., Science, 1991, 254, 1497-1500).

It is also possible to link other types of molecules (conjugates) to nucleotides or nucleotide analogs. Conjugates can be chemically linked to the nucleotide or nucleotide analogs. Such conjugates include but are not limited to lipid moieties such as a cholesterol moiety (Letsinger et al., Proc. Natl. Acad. Sci. USA, 1989, 86, 6553-6556), cholic acid (Manoharan et al., Bioorg. Med. Chem. Let., 1994, 4, 1053-1060), a thioether, e.g., hexyl-5-tritylthiol (Manoharan et al., Ann. N.Y. Acad. Sci., 1992, 660, 306-309; Manoharan et al., Bioorg. Med. Chem. Let., 1993, 3, 2765-2770), a thiocholesterol (Oberhauser et al., Nucl. Acids Res., 1992, 20, 533-538), an aliphatic chain, e.g., dodecandiol or undecyl residues (Saison-Behmoaras et al., EMBO J., 1991, 10, 1111-1118; Kabanov et al., FEBS Lett., 1990, 259, 327-330; Svinarchuk et al., Biochimie, 1993, 75, 49-54), a phospholipid, e.g., dihexadecyl-rac-glycerol or triethylammonium 1,2-di-O-hexadecyl-rac-glycero-3-H-phosphonate (Manoharan et al., Tetrahedron Lett., 1995, 36, 3651-3654; Shea et al., Nucl. Acids Res., 1990, 18, 3777-3783), a polyamine or a polyethylene glycol chain (Manoharan et al., Nucleosides & Nucleotides, 1995, 14, 969-973), or adamantane acetic acid (Manoharan et al., Tetrahedron Lett., 1995, 36, 3651-3654), a palmityl moiety (Mishra et al., Biochim. Biophys. Acta, 1995, 1264, 229-237), or an octadecylamine or hexylamino-carbonyl-oxycholesterol moiety (Crooke et al., J. Pharmacol. Exp. Ther., 1996, 277, 923-937). Numerous U.S. patents teach the preparation of such conjugates and include, but are not limited to U.S. Pat. Nos. 4,828,979; 4,948,882; 5,218,105; 5,525,465; 5,541,313; 5,545,730; 5,552,538; 5,578,717, 5,580,731; 5,580,731; 5,591,584; 5,109,124; 5,118,802; 5,138,045; 5,414,077; 5,486,603; 5,512,439; 5,578,718; 5,608,046; 4,587,044; 4,605,735; 4,667,025; 4,762,779; 4,789,737; 4,824,941; 4,835,263; 4,876,335; 4,904,582; 4,958,013; 5,082,830; 5,112,963; 5,214,136; 5,082,830; 5,112,963; 5,214,136; 5,245,022; 5,254,469; 5,258,506; 5,262,536; 5,272,250; 5,292,873; 5,317,098; 5,371,241; 5,391,723; 5,416,203; 5,451,463; 5,510,475; 5,512,667; 5,514,785; 5,565,552; 5,567,810; 5,574,142; 5,585,481; 5,587,371; 5,595,726; 5,597,696; 5,599,923; 5,599,928 and 5,688,941, each of which is herein incorporated by reference.

A Watson-Crick interaction is at least one interaction with the Watson-Crick face of a nucleotide, nucleotide analog, or nucleotide substitute. The Watson-Crick face of a nucleotide, nucleotide analog, or nucleotide substitute includes the C2, N1, and C6 positions of a purine based nucleotide, nucleotide analog, or nucleotide substitute and the C2, N3, C4 positions of a pyrimidine based nucleotide, nucleotide analog, or nucleotide substitute.

A Hoogsteen interaction is the interaction that takes place on the Hoogsteen face of a nucleotide or nucleotide analog, which is exposed in the major groove of duplex DNA. The Hoogsteen face includes the N7 position and reactive groups (NH2 or O) at the C6 position of purine nucleotides.

C. Primers and Probes

Disclosed are compositions including primers and probes, which are capable of interacting with the disclosed nucleic acids, such as the model oligotriplex as disclosed herein. In certain embodiments the primers are used to support nucleic acid extension reactions, nucleic acid replication reactions, and/or nucleic acid amplification reactions. Typically the primers will be capable of being extended in a sequence specific manner. Extension of a primer in a sequence specific manner includes any methods wherein the sequence and/or composition of the nucleic acid molecule to which the primer is hybridized or otherwise associated directs or influences the composition or sequence of the product produced by the extension of the primer. Extension of the primer in a sequence specific manner therefore includes, but is not limited to, PCR, DNA sequencing, DNA extension, DNA polymerization, RNA transcription, or reverse transcription. Techniques and conditions that amplify the primer in a sequence specific manner are preferred. In certain embodiments the primers are used for the DNA amplification reactions, such as PCR or direct sequencing. It is understood that in certain embodiments the primers can also be extended using non-enzymatic techniques, where for example, the nucleotides or oligonucleotides used to extend the primer are modified such that they will chemically react to extend the primer in a sequence specific manner. Typically the disclosed primers hybridize with the disclosed nucleic acids or region of the nucleic acids or they hybridize with the complement of the nucleic acids or complement of a region of the nucleic acids. As an example of the use of primers, one or more primers can be used to create extension products from and templated by a first nucleic acid.

The size of the primers or probes for interaction with the nucleic acids can be any size that supports the desired enzymatic manipulation of the primer, such as DNA amplification or the simple hybridization of the probe or primer. A typical primer or probe would be at least 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 125, 150, 175, 200, 225, 250, 275, 300, 325, 350, 375, 400, 425, 450, 475, 500, 550, 600, 650, 700, 750, 800, 850, 900, 950, 1000, 1250, 1500, 1750, 2000, 2250, 2500, 2750, 3000, 3500, or 4000 nucleotides long.

In other embodiments a primer or probe can be less than or equal to 6, 7, 8, 9, 10, 11, 12 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 125, 150, 175, 200, 225, 250, 275, 300, 325, 350, 375, 400, 425, 450, 475, 500, 550, 600, 650, 700, 750, 800, 850, 900, 950, 1000, 1250, 1500, 1750, 2000, 2250, 2500, 2750, 3000, 3500, or 4000 nucleotides long.

The primers for the nucleic acid of interest typically will be used to produce extension products and/or other replicated or amplified products that contains a region of the nucleic acid of interest. The size of the product can be such that the size can be accurately determined to within 3, or 2 or 1 nucleotides.

In certain embodiments the product can be, for example, at least 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 125, 150, 175, 200, 225, 250, 275, 300, 325, 350, 375, 400, 425, 450, 475, 500, 550, 600, 650, 700, 750, 800, 850, 900, 950, 1000, 1250, 1500, 1750, 2000, 2250, 2500, 2750, 3000, 3500, or 4000 nucleotides long.

In other embodiments the product can be, for example, less than or equal to 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 125, 150, 175, 200, 225, 250, 275, 300, 325, 350, 375, 400, 425, 450, 475, 500, 550, 600, 650, 700, 750, 800, 850, 900, 950, 1000, 1250, 1500, 1750, 2000, 2250, 2500, 2750, 3000, 3500, or 4000 nucleotides long.

1. Fluorescent Change Probes and Primers

Fluorescent change probes and fluorescent change primers refer to all probes and primers that involve a change in fluorescence intensity or wavelength based on a change in the form or conformation of the probe or primer and nucleic acid to be detected, assayed or replicated. Examples of fluorescent change probes and primers include molecular beacons, Amplifluors, FRET probes, cleavable FRET probes, TaqMan probes, scorpion primers, fluorescent triplex oligos including but not limited to triplex molecular beacons or triplex FRET probes, fluorescent water-soluble conjugated polymers, PNA probes and QPNA probes.

Fluorescent change probes and primers can be classified according to their structure and/or function. Fluorescent change probes include hairpin quenched probes, cleavage quenched probes, cleavage activated probes, and fluorescent activated probes. Fluorescent change primers include stem quenched primers and hairpin quenched primers. The use of several types of fluorescent change probes and primers are reviewed in Schweitzer and Kingsmore, Curr. Opin. Biotech. 12:21-27 (2001). Hall et al., Proc. Natl. Acad. Sci. USA 97:8272-8277 (2000), describe the use of fluorescent change probes with Invader assays.

Hairpin quenched probes are probes that when not bound to a target sequence form a hairpin structure (and, typically, a loop) that brings a fluorescent label and a quenching moiety into proximity such that fluorescence from the label is quenched. When the probe binds to a target sequence, the stem is disrupted, the quenching moiety is no longer in proximity to the fluorescent label and fluorescence increases. Examples of hairpin quenched probes are molecular beacons, fluorescent triplex oligos, triplex molecular beacons, triplex FRET probes, and QPNA probes.

Cleavage activated probes are probes where fluorescence is increased by cleavage of the probe. Cleavage activated probes can include a fluorescent label and a quenching moiety in proximity such that fluorescence from the label is quenched. When the probe is clipped or digested (typically by the 5'-3' exonuclease activity of a polymerase during amplification), the quenching moiety is no longer in proximity to the fluorescent label and fluorescence increases. TaqMan probes (Holland et al., Proc. Natl. Acad. Sci. USA 88:7276-7280 (1991)) are an example of cleavage activated probes.

Cleavage quenched probes are probes where fluorescence is decreased or altered by cleavage of the probe. Cleavage quenched probes can include an acceptor fluorescent label and a donor moiety such that, when the acceptor and donor are in proximity, fluorescence resonance energy transfer from the donor to the acceptor causes the acceptor to fluoresce. The probes are thus fluorescent, for example, when hybridized to a target sequence. When the probe is clipped or digested (typically by the 5'-3' exonuclease activity of a polymerase during amplification), the donor moiety is no longer in proximity to the acceptor fluorescent label and fluorescence from the acceptor decreases. If the donor moiety is itself a fluorescent label, it can release energy as fluorescence (typically at a different wavelength than the fluorescence of the acceptor) when not in proximity to an acceptor. The overall effect would then be a reduction of acceptor fluorescence and an increase in donor fluorescence. Donor fluorescence in the case of cleavage quenched probes is equivalent to fluorescence generated by cleavage activated probes with the acceptor being the quenching moiety and the donor being the fluorescent label. Cleavable FRET (fluorescence resonance energy transfer) probes are an example of cleavage quenched probes.

Fluorescent activated probes are probes or pairs of probes where fluorescence is increased or altered by hybridization of the probe to a target sequence. Fluorescent activated probes can include an acceptor fluorescent label and a donor moiety such that, when the acceptor and donor are in proximity (when the probes are hybridized to a target sequence), fluorescence resonance energy transfer from the donor to the acceptor causes the acceptor to fluoresce. Fluorescent activated probes are typically pairs of probes designed to hybridize to adjacent sequences such that the acceptor and donor are brought into proximity. Fluorescent activated probes can also be single probes containing both a donor and acceptor where, when the probe is not hybridized to a target sequence, the donor and acceptor are not in proximity but where the donor and acceptor are brought into proximity when the probe hybridized to a target sequence. This can be accomplished, for example, by placing the donor and acceptor on opposite ends of the probe and placing target complement sequences at each end of the probe where the target complement sequences are complementary to adjacent sequences in a target sequence. If the donor moiety of a fluorescent activated probe is itself a fluorescent label, it can release energy as fluorescence (typically at a different wavelength than the fluorescence of the acceptor) when not in proximity to an acceptor (that is, when the probes are not hybridized to the target sequence). When the probes hybridize to a target sequence, the overall effect would then be a reduction of donor fluorescence and an increase in acceptor fluorescence. FRET probes are an example of fluorescent activated probes.

Stem quenched primers are primers that when not hybridized to a complementary sequence form a stem structure (either an intramolecular stem structure or an intermolecular stem structure) that brings a fluorescent label and a quenching moiety into proximity such that fluorescence from the label is quenched. When the primer binds to a complementary sequence, the stem is disrupted, the quenching moiety is no longer in proximity to the fluorescent label and fluorescence increases. In the disclosed method, stem quenched primers are used as primers for nucleic acid synthesis and thus become incorporated into the synthesized or amplified nucleic acid. Examples of stem quenched primers are peptide nucleic acid quenched primers and hairpin quenched primers.

Peptide nucleic acid quenched primers are primers associated with a peptide nucleic acid quencher or a peptide nucleic acid fluor to form a stem structure. The primer contains a fluorescent label or a quenching moiety and is associated with either a peptide nucleic acid quencher or a peptide nucleic acid fluor, respectively. This puts the fluorescent label in proximity to the quenching moiety. When the primer is replicated, the peptide nucleic acid is displaced, thus allowing the fluorescent label to produce a fluorescent signal.

Hairpin quenched primers are primers that when not hybridized to a complementary sequence form a hairpin structure (and, typically, a loop) that brings a fluorescent label and a quenching moiety into proximity such that fluorescence from the label is quenched. When the primer binds to a complementary sequence, the stem is disrupted, the quenching moiety is no longer in proximity to the fluorescent label and fluorescence increases. Hairpin quenched primers are typically used as primers for nucleic acid synthesis and thus become incorporated into the synthesized or amplified nucleic acid. Examples of hairpin quenched primers are Amplifluor primers (Nazerenko et al., Nucleic Acids Res. 25:2516-2521 (1997)) and scorpion primers (Thelwell et al., Nucleic Acids Res. 28(19):3752-3761 (2000)).

Cleavage activated primers are similar to cleavage activated probes except that they are primers that are incorporated into replicated strands and are then subsequently cleaved. Little et al., Clin. Chem. 45:777-784 (1999), describe the use of cleavage activated primers.

D. Labels

To aid in detection and quantitation of nucleic acids produced using the disclosed methods, labels can be directly incorporated into nucleotides and nucleic acids or can be coupled to detection molecules such as probes and primers. As used herein, a label is any molecule that can be associated with a nucleotide or nucleic acid, directly or indirectly, and which results in a measurable, detectable signal, either directly or indirectly. Many such labels for incorporation into nucleotides and nucleic acids or coupling to nucleic acid probes are known to those of skill in the art. Examples of labels suitable for use in the disclosed method are radioactive isotopes, fluorescent molecules, phosphorescent molecules, enzymes, antibodies, and ligands. Fluorescent labels, especially in the context of fluorescent change probes and primers, are useful for real-time detection of amplification.

Examples of suitable fluorescent labels include fluorescein isothiocyanate (FITC), 5,6-carboxymethyl fluorescein, Texas red, nitrobenz-2-oxa-1,3-diazol-4-yl (NBD), coumarin, dansyl chloride, rhodamine, amino-methyl coumarin (AMCA), Eosin, Erythrosin, BODIPY®, Cascade Blue®, Oregon Green®, pyrene, lissamine, xanthenes, acridines, oxazines, phycoerythrin, macrocyclic chelates of lanthanide ions such as Quantum Dye™, fluorescent energy transfer dyes, such as thiazole orange-ethidium heterodimer, and the cyanine dyes Cy3, Cy3.5, Cy5, Cy5.5 and Cy7. Examples of other specific fluorescent labels include 3-Hydroxypyrene 5,8,10-Tri Sulfonic acid, 5-Hydroxy Tryptamine (5-HT), Acid Fuchsin, Alizarin Complexon, Alizarin Red, Allophycocyanin, Aminocoumarin, Anthroyl Stearate, Astrazon Brilliant Red 4G, Astrazon Orange R, Astrazon Red 6B, Astrazon Yellow 7 GLL, Atabrine, Auramine, Aurophosphine, Aurophosphine G, BAO 9 (Bisaminophenyloxadiazole), BCECF, Berberine Sulphate, Bisbenzamide, Blancophor FFG Solution, Blancophor SV, Bodipy F1, Brilliant Sulphoflavin FF, Calcien Blue, Calcium Green, Calcofluor RW Solution, Calcofluor White, Calcophor White ABT Solution, Calcophor White Standard Solution, Carbostyryl, Cascade Yellow, Catecholamine, Chinacrine, Coriphosphine O, Coumarin-Phalloidin, CY3.18, CY5.18, CY7, Dans (1-Dimethyl Amino Naphaline 5 Sulphonic Acid), Dansa (Diamino Naphtyl Sulphonic Acid), Dansyl NH—CH3, Diamino Phenyl Oxydiazole (DAO), Dimethylamino-5-Sulphonic acid, Dipyrrometheneboron Difluoride, Diphenyl Brilliant Flavine 7GFF, Dopamine, Erythrosin ITC, Euchrysin, FIF (Formaldehyde Induced Fluorescence), Flazo Orange, Fluo 3, Fluorescamine, Fura-2, Genacryl Brilliant Red B, Genacryl Brilliant Yellow 10GF, Genacryl Pink 3G, Genacryl Yellow 5GF, Gloxalic Acid, Granular Blue, Haematoporphyrin, Indo-1, Intrawhite Cf Liquid, Leucophor PAF, Leucophor SF, Leucophor WS, Lissamine Rhodamine B200 (RD200), Lucifer Yellow CH, Lucifer Yellow VS, Magdala Red, Marina Blue, Maxilon Brilliant Flavin 10 GFF, Maxilon Brilliant Flavin 8 GFF, MPS (Methyl Green Pyronine Stilbene), Mithramycin, NBD Amine, Nitrobenzoxadidole, Noradrenaline, Nuclear Fast Red, Nuclear Yellow, Nylosan Brilliant Flavin E8G, Oxadiazole, Pacific Blue, Pararosaniline (Feulgen), Phorwite AR Solution, Phorwite BKL, Phorwite Rev, Phorwite RPA, Phosphine 3R, Phthalocyanine, Phycoerythrin R, Phycoerythrin B, Polyazaindacene Pontochrome Blue Black, Porphyrin, Primuline, Procion Yellow, Pyronine, Pyronine B, Pyrozal Brilliant Flavin 7GF, Quinacrine Mustard, Rhodamine 123, Rhodamine 5 GLD, Rhodamine 6G, Rhodamine B, Rhodamine B 200, Rhodamine B Extra, Rhodamine BB, Rhodamine BG, Rhodamine WT, Serotonin, Sevron Brilliant Red 2B, Sevron Brilliant Red 4G, Sevron Brilliant Red B, Sevron Orange, Sevron Yellow L, SITS (Primuline), SITS (Stilbene Isothiosulphonic acid), Stilbene, Snarf 1, sulpho Rhodamine B Can C, Sulpho Rhodamine G Extra, Tetracycline, Thiazine Red R, Thioflavin S, Thioflavin TCN, Thioflavin 5, Thiolyte, Thiozol Orange, Tinopol CBS, True Blue, Ultralite, Uranine B, Uvitex SFC, Xylene Orange, and XRITC.

Preferred fluorescent labels are fluorescein (5-carboxyfluorescein-N-hydroxysuccinimide ester), rhodamine (5,6-tetramethyl rhodamine), and the cyanine dyes Cy3, Cy3.5, Cy5, Cy5.5 and Cy7. The absorption and emission maxima, respectively, for these fluors are: FITC (490 nm; 520 nm), Cy3 (554 nm; 568 nm), Cy3.5 (581 nm; 588 nm), Cy5 (652 nm: 672 nm), Cy5.5 (682 nm; 703 nm) and Cy7 (755 nm; 778 nm), thus allowing their simultaneous detection. Other examples of fluorescein dyes include 6-carboxyfluorescein (6-FAM), 2',4',1,4,-tetrachlorofluorescein (TET), 2',4',5',7',1, 4-hexachlorofluorescein (HEX), 2',7'-dimethoxy-4',5'-dichloro-6-carboxyrhodamine (JOE), 2'-chloro-5'-fluoro-7', 8'-fused phenyl-1,4-dichloro-6-carboxyfluorescein (NED), and 2'-chloro-7'-phenyl-1,4-dichloro-6-carboxyfluorescein (VIC). Fluorescent labels can be obtained from a variety of commercial sources, including Amersham Pharmacia Biotech, Piscataway, N.J.; Molecular Probes, Eugene, Oreg.; and Research Organics, Cleveland, Ohio.

Additional labels of interest include those that provide for signal only when the probe with which they are associated is specifically bound to a target molecule, where such labels include: "molecular beacons" as described in Tyagi & Kramer, Nature Biotechnology (1996) 14:303 and EP 0 070 685 B1. Other labels of interest include those described in U.S. Pat. No. 5,563,037; WO 97/17471 and WO 97/17076.

Labeled nucleotides are a preferred form of label since they can be directly incorporated into the amplification products during synthesis. Examples of labels that can be incorporated into amplified nucleic acids include nucleotide analogs such as BrdUrd (5-bromodeoxyuridine, Hoy and Schimke, *Mutation Research* 290:217-230 (1993)), aminoallyldeoxyuridine (Henegariu et al., *Nature Biotechnology* 18:345-348 (2000)), 5-methylcytosine (Sano et al., *Biochim. Biophys. Acta* 951: 157-165 (1988)), bromouridine (Wansick et al., *J. Cell Biology* 122:283-293 (1993)) and nucleotides modified with biotin (Langer et al., *Proc. Natl. Acad. Sci. USA* 78:6633 (1981)) or with suitable haptens such as digoxygenin (Kerkhof, *Anal. Biochem.* 205:359-364 (1992)). Suitable fluorescence-labeled nucleotides are Fluorescein-isothiocyanate-dUTP, Cyanine-3-dUTP and Cyanine-5-dUTP (Yu et al., *Nucleic Acids Res.,* 22:3226-3232 (1994)). A preferred nucleotide analog label for DNA is BrdUrd (bromodeoxyuridine, BrdUrd, BrdU, BUdR, Sigma-Aldrich Co). Other preferred nucleotide analogs for incorporation of label into DNA are AA-dUTP (aminoallyl-deoxyuridine triphosphate, Sigma-Aldrich Co.), and 5-methyl-dCTP (Roche Molecular Biochemicals). A preferred nucleotide analog for incorporation of label into RNA is biotin-16-UTP (biotin-16-uridine-5'-triphosphate, Roche Molecular Biochemicals). Fluorescein, Cy3, and Cy5 can be linked to dUTP for direct labeling. Cy3.5 and Cy7 are available as avidin or anti-digoxygenin conjugates for secondary detection of biotin- or digoxygenin-labeled probes.

Labels that are incorporated into amplified nucleic acid, such as biotin, can be subsequently detected using sensitive methods well-known in the art. For example, biotin can be detected using streptavidin-alkaline phosphatase conjugate (Tropix, Inc.), which is bound to the biotin and subsequently detected by chemiluminescence of suitable substrates (for example, chemiluminescent substrate CSPD: disodium, 3-(4-methoxyspiro-[1,2,-dioxetane-3-2'-(5'-chloro)tricyclo [$3.3.1.1^{3,7}$]decane]-4-yl)phenyl phosphate; Tropix, Inc.). Labels can also be enzymes, such as alkaline phosphatase, soybean peroxidase, horseradish peroxidase and polymerases, that can be detected, for example, with chemical signal amplification or by using a substrate to the enzyme which produces light (for example, a chemiluminescent 1,2-dioxetane substrate) or fluorescent signal.

Molecules that combine two or more of these labels are also considered labels. Any of the known labels can be used with the disclosed probes, tags, and method to label and detect nucleic acid amplified using the disclosed method. Methods for detecting and measuring signals generated by labels are also known to those of skill in the art. For example, radioactive isotopes can be detected by scintillation counting or direct visualization; fluorescent molecules can be detected with fluorescent spectrophotometers; phosphorescent molecules can be detected with a spectrophotometer or directly visualized with a camera; enzymes can be detected by detection or visualization of the product of a reaction catalyzed by the enzyme; antibodies can be detected by detecting a secondary label coupled to the antibody. As used herein, detection molecules are molecules which interact with amplified nucleic acid and to which one or more labels are coupled.

E. Sequence Similarities

It is understood that as discussed herein the use of the terms homology and identity mean the same thing as similarity. Thus, for example, if the use of the word homology is used between two non-natural sequences it is understood that this is not necessarily indicating an evolutionary relationship between these two sequences, but rather is looking at the similarity or relatedness between their nucleic acid sequences. Many of the methods for determining homology between two evolutionarily related molecules are routinely applied to any two or more nucleic acids or proteins for the purpose of measuring sequence similarity regardless of whether they are evolutionarily related or not.

In general, it is understood that one way to define any known variants and derivatives or those that might arise, of the disclosed genes and proteins herein, is through defining the variants and derivatives in terms of homology to specific known sequences. This identity of particular sequences disclosed herein is also discussed elsewhere herein. In general, variants of genes and proteins herein disclosed typically have at least, about 70, 71, 72, 73, 74, 75, 76, 77, 78, 79, 80, 81, 82, 83, 84, 85, 86, 87, 88, 89, 90, 91, 92, 93, 94, 95, 96, 97, 98, or 99 percent homology to the stated sequence or the native sequence. Those of skill in the art readily understand how to determine the homology of two proteins or nucleic acids, such as genes. For example, the homology can be calculated after aligning the two sequences so that the homology is at its highest level.

Another way of calculating homology can be performed by published algorithms. Optimal alignment of sequences for comparison may be conducted by the local homology algorithm of Smith and Waterman Adv. Appl. Math. 2: 482 (1981), by the homology alignment algorithm of Needleman and Wunsch, *J. Mol. Biol.* 48: 443 (1970), by the search for similarity method of Pearson and Lipman, *Proc. Natl. Acad. Sci. U.S.A.* 85: 2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by inspection.

The same types of homology can be obtained for nucleic acids by for example the algorithms disclosed in Zuker, M. *Science* 244:48-52, 1989, Jaeger et al. *Proc. Natl. Acad. Sci. USA* 86:7706-7710, 1989, Jaeger et al. *Methods Enzymol.* 183:281-306, 1989 which are herein incorporated by reference for at least material related to nucleic acid alignment. It is understood that any of the methods typically can be used and that in certain instances the results of these various methods may differ, but the skilled artisan understands if identity is found with at least one of these methods, the sequences would be said to have the stated identity, and be disclosed herein.

For example, as used herein, a sequence recited as having a particular percent homology to another sequence refers to sequences that have the recited homology as calculated by any one or more of the calculation methods described above. For example, a first sequence has 80 percent homology, as defined herein, to a second sequence if the first sequence is calculated to have 80 percent homology to the second sequence using the Zuker calculation method even if the first sequence does not have 80 percent homology to the second sequence as calculated by any of the other calculation methods. As another example, a first sequence has 80 percent homology, as defined herein, to a second sequence if the first sequence is calculated to have 80 percent homology to the second sequence using both the Zuker calculation method and the Pearson and Lipman calculation method even if the first sequence does not have 80 percent homology to the second sequence as calculated by the Smith and Waterman calculation method, the Needleman and Wunsch calculation method, the Jaeger calculation methods, or any of the other calculation methods. As yet another example, a first sequence has 80 percent homology, as defined herein, to a second sequence if the first sequence is calculated to have 80 percent homology to the second sequence using each of calculation methods (although, in practice, the different calculation methods will often result in different calculated homology percentages).

F. Hybridization/Selective Hybridization

The term hybridization typically means a sequence driven interaction between at least two nucleic acid molecules, such as a primer or a probe and a gene. Sequence driven interaction means an interaction that occurs between two nucleotides or nucleotide analogs or nucleotide derivatives in a nucleotide specific manner. For example, G interacting with C or A interacting with T are sequence driven interactions. Typically sequence driven interactions occur on the Watson-Crick face or Hoogsteen face of the nucleotide. The hybridization of two nucleic acids is affected by a number of conditions and parameters known to those of skill in the art. For example, the salt concentrations, pH, and temperature of the reaction all affect whether two nucleic acid molecules will hybridize.

Parameters for selective hybridization between two nucleic acid molecules are well known to those of skill in the art. For example, in some embodiments selective hybridization conditions can be defined as stringent hybridization conditions. For example, stringency of hybridization is controlled by both temperature and salt concentration of either or both of the hybridization and washing steps. For example, the conditions of hybridization to achieve selective hybridization may involve hybridization in high ionic strength solution (6×SSC or 6×SSPE) at a temperature that is about 12-25° C. below the Tm (the melting temperature at which half of the molecules dissociate from their hybridization partners) followed by washing at a combination of temperature and salt concentration chosen so that the washing temperature is about 5° C. to 20° C. below the Tm. The temperature and salt conditions are readily determined empirically in preliminary experiments in which samples of reference DNA immobilized on filters are hybridized to a labeled nucleic acid of interest and then washed under conditions of different stringencies. Hybridization temperatures are typically higher for DNA-RNA and RNA-RNA hybridizations. The conditions can be used as described above to achieve stringency, or as is known in the art. (Sambrook et al., *Molecular Cloning: A Laboratory Manual*, 2nd Ed., Cold Spring Harbor Laboratory, Cold Spring Harbor, N.Y., 1989; Kunkel et al. Methods Enzymol. 1987:154:367, 1987 which is herein incorporated by reference for material at least related to hybridization of nucleic acids). A preferable stringent hybridization condition for a DNA:DNA hybridization can be at about 68° C. (in aqueous solution) in 6×SSC or 6×SSPE followed by washing at 68° C. Stringency of hybridization and washing, if desired, can be reduced accordingly as the degree of complementarity desired is decreased, and further, depending upon the G-C or A-T richness of any area wherein variability is searched for. Likewise, stringency of hybridization and washing, if desired, can be increased accordingly as homology desired is increased, and further, depending upon the G-C or A-T richness of any area wherein high homology is desired, all as known in the art.

Another way to define selective hybridization is by looking at the amount (percentage) of one of the nucleic acids bound to the other nucleic acid. For example, in some embodiments selective hybridization conditions would be when at least about, 60, 65, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100 percent of the limiting nucleic acid is bound to the non-limiting nucleic acid. Typically, the non-limiting primer is in for example, 10 or 100 or 1000 fold excess. This type of assay can be performed at under conditions where both the limiting and non-limiting primer are for example, 10 fold or 100 fold or 1000 fold below their $k_d$, or where only one of the nucleic acid molecules is 10 fold or 100 fold or 1000 fold or where one or both nucleic acid molecules are above their $k_d$.

Another way to define selective hybridization is by looking at the percentage of primer that gets enzymatically manipulated under conditions where hybridization is required to promote the desired enzymatic manipulation. For example, in some embodiments selective hybridization conditions would be when at least about, 60, 65, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100 percent of the primer is enzymatically manipulated under conditions which promote the enzymatic manipulation, for example if the enzymatic manipulation is DNA extension, then selective hybridization conditions would be when at least about 60, 65, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100 percent of the primer molecules are extended. Preferred conditions also include those suggested by the manufacturer or indicated in the art as being appropriate for the enzyme performing the manipulation.

Just as with homology, it is understood that there are a variety of methods herein disclosed for determining the level of hybridization between two nucleic acid molecules. It is understood that these methods and conditions may provide different percentages of hybridization between two nucleic acid molecules, but unless otherwise indicated meeting the parameters of any of the methods would be sufficient. For example if 80% hybridization was required and as long as hybridization occurs within the required parameters in any one of these methods it is considered disclosed herein.

It is understood that those of skill in the art understand that if a composition or method meets any one of these criteria for determining hybridization either collectively or singly it is a composition or method that is disclosed herein.

G. Kits

Disclosed herein are kits that are drawn to reagents that can be used in practicing the methods disclosed herein. The kits can include any reagent or combination of reagent discussed herein or that would be understood to be required or beneficial in the practice of the disclosed methods. For example, the kits could include primers to perform the extension, replication and amplification reactions discussed in certain embodiments of the methods, as well as the buffers and enzymes required to use the primers as intended. Additional reagents could include the modified nucleotides, nuclease-resistant nucleotides, and or labeled nucleotides. The kits can also contain one or more of the agents and/or enzymes to be used in the disclosed methods.

The compositions disclosed herein and the compositions necessary to perform the disclosed methods can be made using any method known to those of skill in the art for that particular reagent or compound unless otherwise specifically noted.

H. Nucleic Acid Synthesis

The disclosed nucleic acids, such as, the oligonucleotides to be used as primers can be made using standard chemical synthesis methods or can be produced using enzymatic methods or any other known method. Such methods can range from standard enzymatic digestion followed by nucleotide fragment isolation (see for example, Sambrook et al., *Molecular Cloning. A Laboratory Manual*, 2nd Edition (Cold Spring Harbor Laboratory Press, Cold Spring Harbor, N.Y., 1989) Chapters 5, 6) to purely synthetic methods, for example, by the cyanoethyl phosphoramidite method using a Milligen or Beckman System 1Plus DNA synthesizer (for example, Model 8700 automated synthesizer of Milligen-Biosearch, Burlington, Mass. or ABI Model 380B). Synthetic methods useful for making oligonucleotides are also described by Ikuta et al., *Ann. Rev. Biochem.* 53:323-356 (1984), (phosphotriester and phosphite-triester methods), and Narang et al., *Methods Enzymol.*, 65:610-620 (1980), (phosphotriester method). Protein nucleic acid molecules can be made using known methods such as those described by Nielsen et al., *Bioconjug. Chem.* 5:3-7 (1994).

EXAMPLES

The following examples are put forth so as to provide those of ordinary skill in the art with a complete disclosure and description of how the compounds, compositions, articles, devices and/or methods claimed herein are made and evaluated, and are intended to be purely exemplary and are not intended to limit the disclosure. Efforts have been made to ensure accuracy with respect to numbers (e.g., amounts, temperature, etc.), but some errors and deviations should be accounted for. Unless indicated otherwise, parts are parts by weight, temperature is in ° C. or is at ambient temperature, and pressure is at or near atmospheric.

A. Example 1

Template Exchange Extension Reaction (TEER)

Template Exchange Extension Reaction (TEER) refers to a class of methods that can compare an unknown or unsequenced nucleic acid template to a sequenced template to determine if they are identical. It is based on the fact that sequencing products are unique to the template from which they are generated. The disclosed methods and compositions involve particular forms of TEER. FIG. 1 shows the extension of 5' biotinylated PCR products on homoduplex or heteroduplex DNA after site specific removal of uracil. A small amount of dUTP relative to the normal dNTPs was used in the PCR to generate a subset of uracil containing amplicons representing each occurrence of thymidine in the sequence. This is essentially a dideoxy T sequencing ladder less the terminal ddT. Extension with all 4 dNTPs (All) shows how the cleaved products are readily extended to full length. Extension with ddUTP (U) extends the ladder out one base with the matching or wildtype nucleotide. The single base extension with either ddGTP(G), ddCTP(C), or ddATP(A) represents possible mutations. The mutation in the heteroduplex is seen in the G lane and is marked with an arrow (<).

Originally the template exchange extension reaction (TEER) was developed to detect unknown germline and somatic mutations present in a homozygous or heterozygous state. This was demonstrated by polyacrylamide gel electrophoresis followed by chemiluminescent detection. The process was converted to a microtiter based detection format. In a microtiter plate format, it has much higher throughput and can be used to quickly screen DNA for mutations prior to DNA sequencing. As a sequence scanning method, it is useful in screening large sample populations where the likelihood of mutation in a particular gene for a given sample was quite low. TEER quickly screens the samples and flags the ones that contained a mutation such that they could be sequenced to identify the mutation.

Figure 2A:
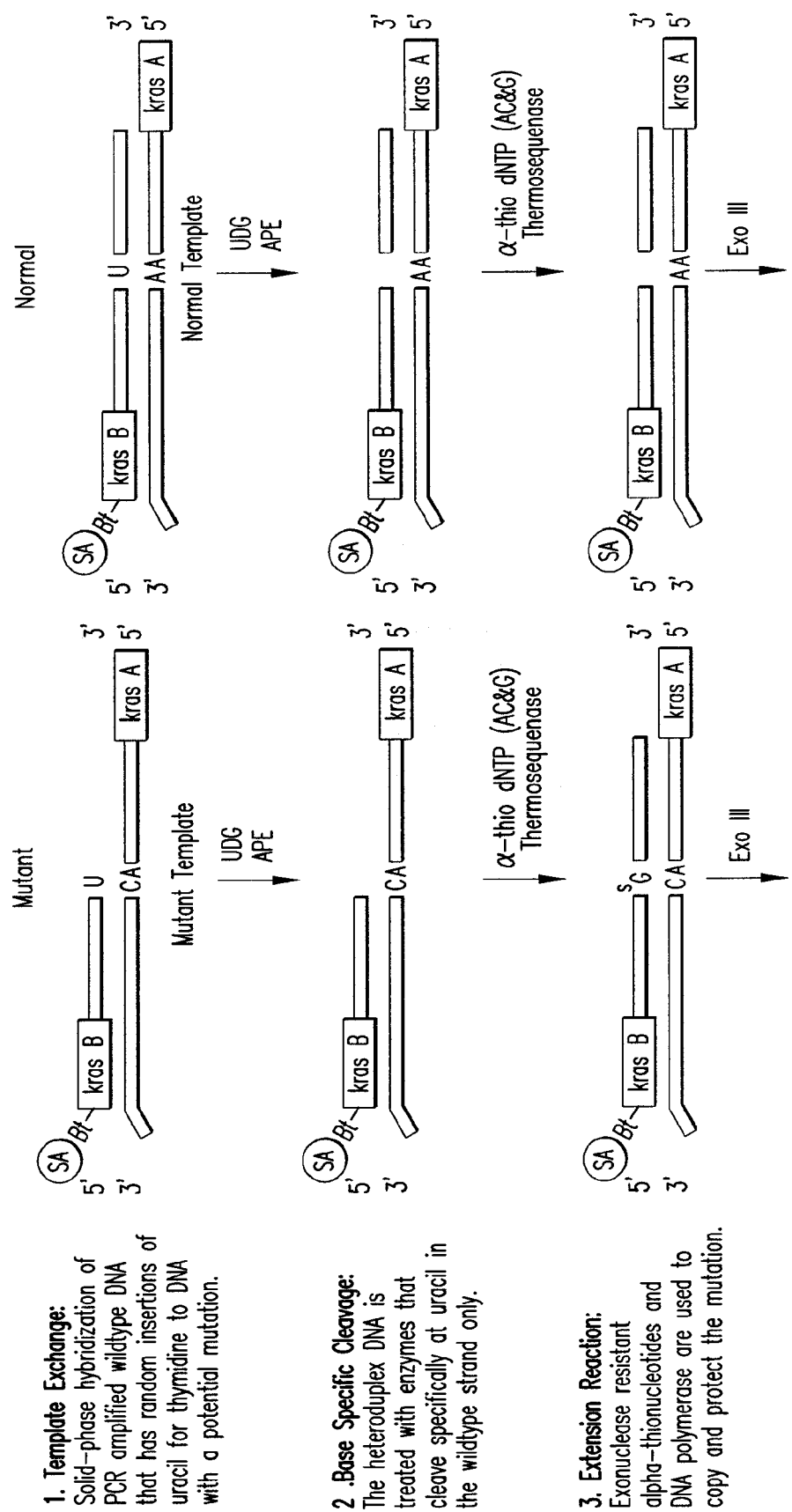
FIG. 2 shows the steps used to detect the extension products in a solid phase microtiter format.

TEER was shown to detect mutations in a microplate format. This was directed toward detecting a known mutation in the kras gene, at either the T or G nucleotide. FIG. 2 shows the steps used to detect the extension products in a solid phase microtiter format. Streptavidin coated microplate wells are used to attach a biotinylated PCR product to the solid phase. Homo and heteroduplex molecules are formed during hybridization in the solid phase. Each step of the process is readily accomplished in the microtiter plate, this greatly simplify sample handling and processing.

The data shown in Table 1 is the average from eight replicate reactions. It shows the increase in signal seen in heteroduplex DNA when the mutation is protected and extended out to the next matching base. Using alpha thionucleotides to protect the mutation, followed by negative selection with exonuclease III, decreased the background and allowed distinction between homoduplex and heteroduplex templates. The next nucleotide in this sequence after the protecting thionucleotide is uracil. Roughly a 4 fold increase in signal of heteroduplex (2158 RLU) over the homoduplex (573 RLU) was achieved when targeting the T nucleotide.

Extension with a mixture of digoxigenin labeled dideoxy NTPs (A, G &C) showed that there was either nonspecific extension by the polymerase or extension from nonspecific enzyme cleavage sites. Nonspecific addition of labeled ddATP to full length template was observed; this activity is commonly seen in Taq polymerases and is the basis of a PCR cloning kit. The amount of DNA in the reaction is roughly the same for the duplexes as demonstrated by the no Exo III control (Row 3). Degradation of matching DNA was seen by the dramatic decrease in extension signal when the duplexes were treated with Exo III (Row 1 &2).

TABLE 1

Microplate Detection of TEER

|  | Exo III | Homoduplex (RLU) | Heteroduplex (RLU) | Change (Het/Hom) |
|---|---|---|---|---|
| dd U-dig | + | 573 | 2158 | 3.8x |
| dd A, G. & C-dig | + | 1345 | 2365 | 1.8x |
| ddU-dig | − | 134,316 | 156,078 | 1.2x |

B. Example 2

Sensitivity of Hybridization

The present methods avoid problems relating to the sensitivity of mutation detection caused by preferential hybridization of highly abundant wildtype DNA to itself over low abundant mutant DNA. While this may be a problem in certain solid phase hybridizations or hybridizations done at temperatures high enough to discriminate homo and heteroduplex DNA, it is not a problem under the conditions being employed. Equal amounts of normal PCR product are mixed with an equal amount of tester DNA. The heteroduplexes are formed by denaturing the samples at 95° C. for 2 min followed by quick cooling to 72° C. and then slow cooled to 40° C. over 30 minutes. Given the size of the PCR products (300 bp) and the non-stringent hybridization conditions (time and temperature), hybridization of wildtype DNA to mutant DNA is not hindered. The hybridization of these two molecules is based on random collision and chance. Since the formation of heteroduplex molecules is not being selected against, the proportion of heteroduplex molecules formed is directly related to the input concentration. If one mutant template is present for every 100 normal templates prior to hybridization, then that ratio will be preserved in the post hybridization products.

C. Example 3

Unknown Mutations

All four nucleotides are targeted to detect unknown mutations. Thymine and guanine nucleotides can be targeted directly. Guanine nucleotides are randomly converted to 8-hydroxyguanine chemically and then excised with FPG and Endo IV. Cytosine and adenine are targeted indirectly by analyzing their complement, guanine and thymine on the opposite strand. It is understood and contemplated herein that other methods can be used to target cytosine and adenine directly and that such methods are compatible with the methods disclosed herein.

For example, while purifying alpha-thio containing PCR products using the Wizard PCR Purification kit from Promega, it was observed that sequencing ladders were being generated specific for each alpha-thionucleotide. The alpha-thionucleotides are sensitive to guanidinum thiocynate, a chaotropic reagent used to bind DNA to silica. This sensitivity to chemical hydrolysis has been well documented with 2-iodoethanol and has been used as a method to sequence DNA. The 3' ends left after cleavage with iodoethanol are a mixture of 3' phosphates and 3' hydroxyl groups. The 3' hydroxyl ends can be readily extended and used in TEER. Thus, this chemical approach can directly and uniformly target each nucleotide.

D. Example 4

Detecting Insertions and Deletions

TEER can readily detect insertion and deletions. These mutations create a mismatch at the point of the insertion/deletion or just 3' of the mutation (on the wildtype extension strand) where the sequence frame is shifted. Detection of these mutations can be hindered in areas where long stretches of the same nucleotide or repeat sequences are present. For example, when a stretch is sufficiently long a hairpin loop can begin to form such that the insertion or deletion is squeezed out and may not be detected. Insertions or deletions near the middle of these stretches are more problematic to detect than those at the ends.

E. Example 5

Real-Time PCR Detection Of TEER Selected Mutation

During the transition of the chemistry to microplates, it was evident that TEER was selecting for a mutant signal over the normal or wildtype signal. It was generating a signal from one "mutant" out of 60 "normal" single base extensions. The increase in signal of the heteroduplex over homoduplex was not dramatic, about 4 fold, but provided evidence that the process was working. This, along with the need to increase the signal to noise ratio of microplate detection, to the determination of whether PCR could be used to amplify the mutation such that it can be further characterized by DNA sequencing. Utilizing PCR to amplify the mutation first allows for rapid and sensitive detection of rare mutations. Samples that are positive can be sequenced to locate and identify the mutation.

Figure 3A:
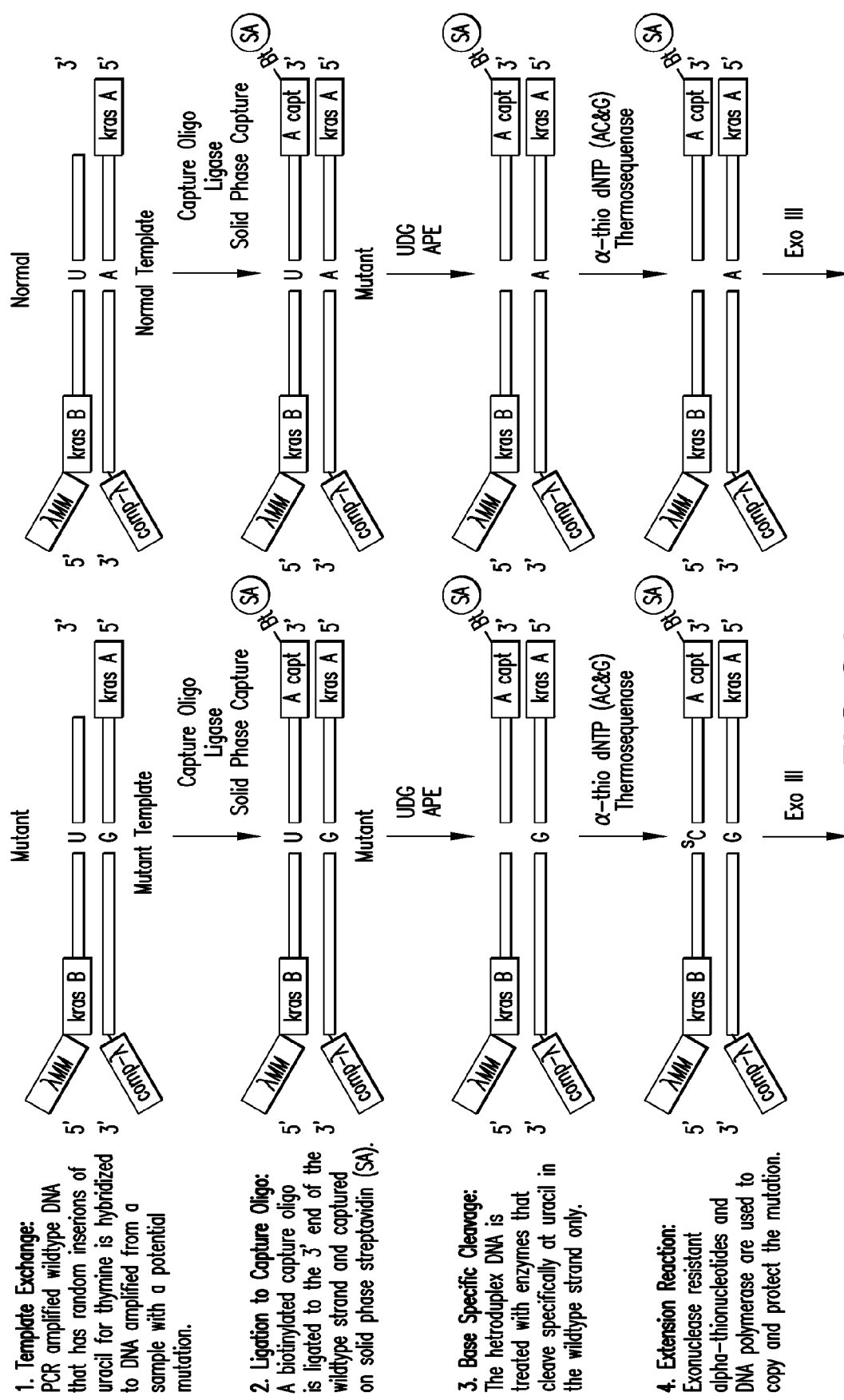
FIG. 3 shows a diagram of an example of the disclosed detection methods utilizing Real-time PCT detection.
Figure 3B:
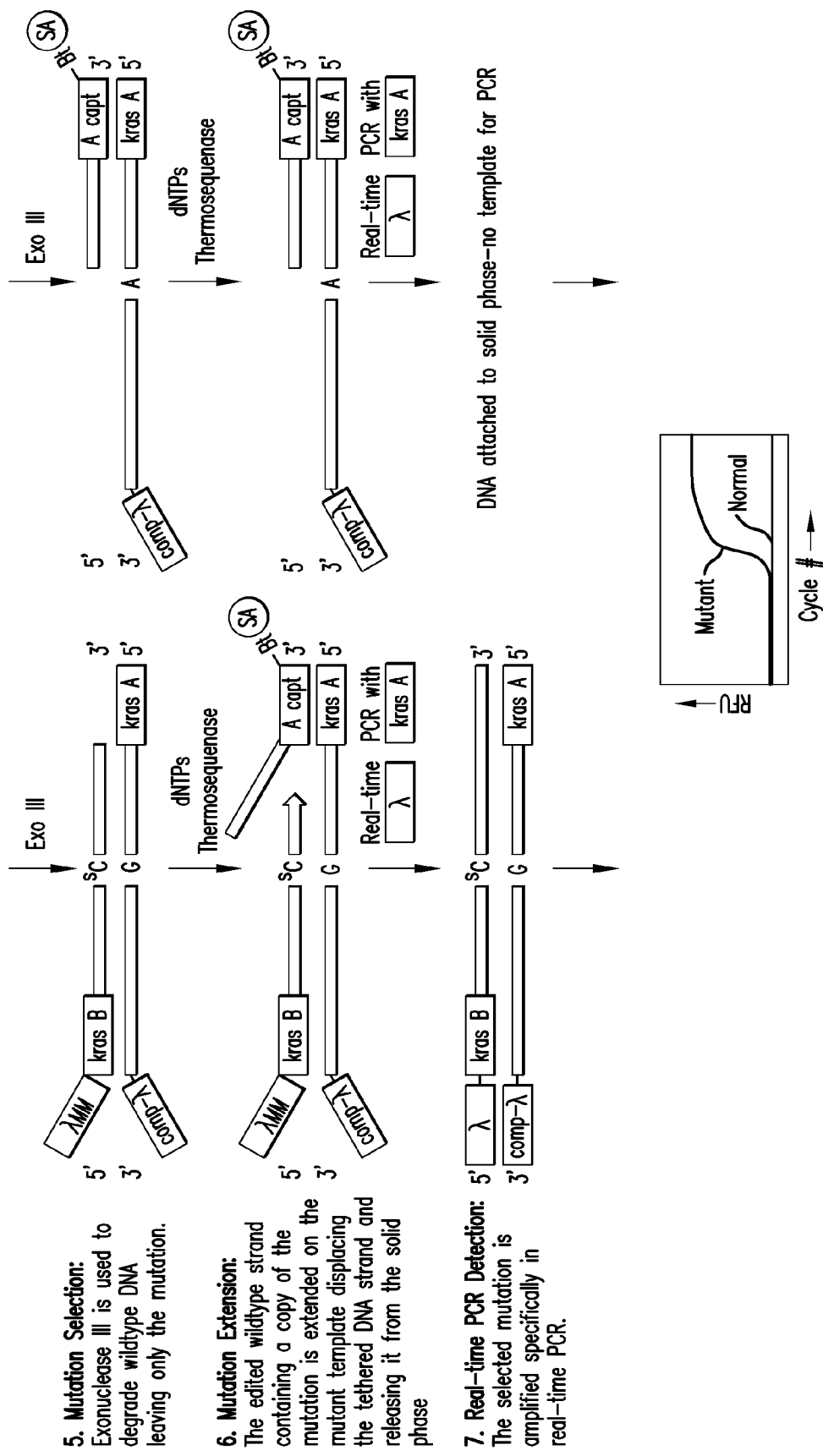

The following description refers to the steps illustrated in FIG. 3. For simplicity, a known mutation in the kras gene is targeted to demonstrate the feasibility of TEER to select for a mutation. This well characterized known mutation is a G to T transition in codon 12. It makes an ideal target to demonstrate that the selection process is working. Thus the feasibility of a realtime PCR detection format to amplify and detect a known single base mutation in kras gene is described. Specifically the targeting of the U nucleotide is illustrated. Each of the remaining 3 bases is targeted in a separate reaction so that each base in the sequence is analyzed. Once TEER selection has taken place, the four reactions products from a sample may be combined together and analyzed in one real-time PCR detection reaction.

The first step in TEER is the template exchange. PCR amplified wildtype DNA that has been modified randomly at a specific base is hybridized to DNA amplified from a sample with a potential mutation. The duplex DNA has mismatches at one end to prevent degradation with Exo III and the opposite end has a 3' recessed end to allow ligation of a linker probe for solid phase attachment. The linker ensures that all of the target is hybridized to its complement and that it is a full length extension product. Any incomplete extension products will not be ligated and will be readily removed from the plate by using a stringent wash. The heteroduplex DNA is treated with enzymes or chemicals that cleave specifically at the modified nucleotide (uracil) in the wildtype strand only. The complementary strand potentially containing a mutation is not affected. This creates a subset of abasic sites representative of each occurrence of the base in the sequence. This is essentially a sequencing ladder, less the targeted base, on an intact full-length template.

The next step in TEER is an extension reaction with exonuclease resistant nucleotides. Here alpha-thionucleotides are being used (Pincas H, et al. *Nucleic Acids Res* 2004; 32(19):e148; Nakamaye K L, et al. *Nucleic Acids Res* 1988; 16(21):9947-59; Labeit S, et al. *Methods Enzymol* 1987; 155: 166-77; Labeit S, et al. *DNA* 1986; 5(2):173-7). It is understood and herein contemplated that Boron nucleotides can also be used (Porter K W, et al. *Nucleic Acids Res* 1997; 25(8):1611-7). A mixture of three alpha-thio deoxynucleotide triphosphates (dNTPs) that represent the three possible nucleotide mutations, are used in the extension reaction with Thermosequenase. A dNTP matching the targeted base is not present. For example, when thymine (via uracil) was the targeted base, then the extension nucleotides would be alpha-thio dATP, dCTP, and dGTP.

Exonuclease III can be used to select for mutations. Extension products terminated with thionucleotides represent mutations and are resistant to exonuclease III. Unprotected wildtype template is degraded.

The edited wildtype strand now contains a copy of the mutation. As the polymerase extends the DNA it uses strand displacement, or a 5' to 3' exonuclease depending on the polymerase, to advance to the end of the mutant template. This process releases the mutant duplex from the solid phase. The released DNA can be transferred from the microplate directly into a realtime PCR reaction.

The selected mutant template is amplified specifically using a real-time fluorescent forward primer and reverse primer. For example, SYBR green dye or a fluorogenic hairpin primer that fluoresces only after it has been extended such as a LUX primer (Invitrogen, Carlsbad, Calif.) can be used. The use of internal hybridizing probes for real-time PCR such as Taqman or dual labeled FRET probes is not recommended since the site of the mutation is not known.

F. Example 6

Model Triplex

In order to monitor and optimize each step in the process, an oligo hybrid composed of 3 oligonucleotides can be used (FIG. 4). The oligotriplex is a miniature version of the full products less the intervening sequence. The LamMM-krasB has a 5'FAM label to allow detection of extension/ligation products by capillary gel electrophoresis. The upper construct creates a nick whereas the bottom construct has a gap. Using this method, various polymerases and ligases can be studied for their ability to initiate activity at either site. The efficiency of solid phase capture and release can also be studied There are a number of conditions that need to be optimized for each step in the process. The oligotriplex helps in the optimization each of these steps. There are number of technical risk in this model that will affect mutation selection specificity. Exonuclease III digestion has to be very efficient only leaving 3' ends terminated with alpha-thionucleotides. Any incomplete digestion products cause background in the real-time PCR. Optimizing time, concentration and buffer conditions for this reaction are important to keeping background low.

Also cleavage with UDG and APE must be highly specific. Any random or nonspecific cleavage will create background. Again, optimizing time, concentration and buffer conditions for this reaction will be critical to keeping background low. The enzymes in optimized conditions are very specific. DNA ligase can be used to resolve any nonspecific nicking.

At least a 10 cycle difference can be observed between the homoduplex DNA and heteroduplex. This is a 50:50 mix or 1:2 ratio of mutant to wildtype. Thus, at least a 1:100 dilution of the mutation can be detected. Using the method illustrated in FIG. 3 above, a 4 cycle decrease in average crossing points for heteroduplex DNA versus homoduplex DNA was observed. For a background control, different combinations of hetero and homoduplex products were tested. Both heteroduplex have a G:T mismatch, but are the reverse complement of each other. The heteroduplex SW/K5 has the targeted nucleotide (T via uracil) on the proper strand for detection. The background crossing points were higher than expected, as evidenced by the low crossing points. Also the standard deviation between replicate amplification of the same TEER product were quite high. This is surprising based on the high (3.33) amplification efficiency the SYBR green real-time PCR. The assay was optimized using a 10 fold dilution series of highly pure positive template. It is understood that other factors can also be optimized such as the primer concentration annealing temperature/time, extension temperature/time, MgCl2 concentration and primer concentration in the presence of high, low and no template to bring the standard deviation between replicates to less than 0.5.

|  | Avg. Crossing Point (n = 5) | Stnd. Dev. Crossing Point | Delta Homoduplex- Heterpduplex |
|---|---|---|---|
| Homoduplex K5/K5 | 14.6 | 1.63 |  |
| Heteroduplex K5/SW | 15.0 | 1.46 | −0.45 cycles |
| Homoduplex SW/SW | 17.2 | 1.71 |  |
| Heteroduplex SW/K5 | 13.5 | 1.69 | +3.76 cycles |

G. Example 7

Sensitivity of Detection

The ability to detect a known mutation in this model system is important for TEER to detect unknown mutations in DNA. This is a titration experiment where the amount of the mutant kras template is diluted against the normal or wildtype sequence to determine the sensitivity of detection. A dilution series of mutant kras template to normal template is set up at no dilution, 1:2, 1:5, 1:10, 1:50, 1:100 1:500, 1:1000. Reaction conditions are optimized to increase the sensitivity. Preferably, a minimum of 1 mutant template out of 50 normal templates is detected. The quantitative nature of the process will also be evaluated. The ability to quantitate rare unknown mutations relative to normal DNA may establish critical intervention values for cancer treatment and monitoring.

Throughout this application, various publications are referenced. The disclosures of these publications in their entireties are hereby incorporated by reference into this application in order to more fully describe the state of the art to which this invention pertains. The references disclosed are also individually and specifically incorporated by reference herein for the material contained in them that is discussed in the sentence in which the reference is relied upon.

It will be apparent to those skilled in the art that various modifications and variations can be made in the present invention without departing from the scope or spirit of the invention. Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

REFERENCES

Babon J J, McKenzie M, Cotton R G. Mutation detection using fluorescent enzyme mismatch cleavage with T4 endonuclease VII. Electrophoresis 1999; 20(6):1162-70.

Brow M A, Oldenburg M C, Lyamichev V, et al. Differentiation of bacterial 16S rRNA genes and intergenic regions and *Mycobacterium tuberculosis* katG genes by structure-specific endonuclease cleavage. J Clin Microbiol 1996; 34(12):3129-37.

Chen T J, Boles R G, Wong L J. Detection of mitochondrial DNA mutations by temporal temperature gradient gel electrophoresis. Clin Chem 1999; 45(8 Pt 1):1162-7.

Cotton R G, Rodrigues N R, Campbell R D. Reactivity of cytosine and thymine in single-base-pair mismatches with hydroxylamine and osmium tetroxide and its application to the study of mutations. Proc Natl Acad Sci USA 1988; 85(12):4397-401.

Fodde R, Losekoot M. Mutation detection by denaturing gradient gel electrophoresis (DGGE). Hum Mutat 1994; 3(2):83-94.

Ganguly A, Prockop D J. Detection of mismatched bases in double stranded DNA by gel electrophoresis. Electrophoresis 1995; 16(10): 1830-5.

Ganguly A, Rock M J, Prockop D J. Conformation-sensitive gel electrophoresis for rapid detection of single-base differences in double-stranded PCR products and DNA fragments: evidence for solvent-induced bends in DNA heteroduplexes. Proc Natl Acad Sci USA 1993; 90(21):10325-9.

Hacia J G. Resequencing and mutational analysis using oligonucleotide microarrays. Nat Genet. 1999; 21 (I Suppl): 42-7.

Hovig E, Smith-Sorensen B, Brogger A, Borresen A L. Constant denaturant gel electrophoresis, a modification of denaturing gradient gel electrophoresis, in mutation detection. Mutat Res 1991; 262(1):63-71.

Labeit S, Lehrach H, Goody R S. A new method of DNA sequencing using deoxynucleoside alpha-thiotriphosphates. Dna 1986; 5(2):173-7.

Labeit S, Lehrach H, Goody R S. DNA sequencing using alpha-thiodeoxynucleotides. Methods Enzymol 1987; 155:166-77.

Lu A L, Hsu I C. Detection of single DNA base mutations with mismatch repair enzymes. Genomics 1992; 14(2): 249-55.

Myers R M, Larin Z, Maniatis T. Detection of single base substitutions by ribonuclease cleavage at mismatches in RNA:DNA duplexes. Science 1985; 230(4731):1242-6.

Nagamine C M, Chan K, Lau Y F. A PCR artifact: generation of heteroduplexes. Am J Hum Genet. 1989; 45(2):337-9.

Nakamaye K L, Gish G, Eckstein F, Vosberg H P. Direct sequencing of polymerase chain reaction amplified DNA fragments through the incorporation of deoxynucleoside alpha-thiotriphosphates. Nucleic Acids Res 1988; 16(21): 9947-59.

Novack D F, Casna N J, Fischer S G, Ford J P. Detection of single base-pair mismatches in DNA by chemical modification followed by electrophoresis in 15% polyacrylamide gel. Proc Natl Acad Sci USA 1986; 83(3):586-90.

Oldenburg M C, Siebert M. New Cleavase Fragment Length Polymorphism method improves the mutation detection assay. Biotechniques 2000; 28(2):351-7.

Orita M, Suzuki Y, Sekiya T, Hayashi K. Rapid and sensitive detection of point mutations and DNA polymorphisms using the polymerase chain reaction. Genomics 1989; 5(4): 874-9.

Pincas H, Pingle M R, Huang J, et al. High sensitivity EndoV mutation scanning through real-time ligase proofreading. Nucleic Acids Res 2004; 32(19):e148.

Porter K W, Briley J D, Shaw B R. Direct PCR sequencing with boronated nucleotides. Nucleic Acids Res 1997; 25(8):1611-7.

Winter E, Yamamoto F, Almoguera C, Perucho M. A method to detect and characterize point mutations in transcribed genes: amplification and overexpression of the mutant c-Ki-ras allele in human tumor cells. Proc Natl Acad Sci USA 1985; 82(22):7575-9.

Xiao W, Oefner P J. Denaturing high-performance liquid chromatography: A review. Hum Mutat 2001; 17(6):439-74.

Youil R, Kemper B, Cotton R G. Detection of 81 of 81 known mouse beta-globin promoter mutations with T4 endonuclease VII—the EMC method. Genomics 1996; 32:431-5.

It is understood that the disclosed method and compositions are not limited to the particular methodology, protocols, and reagents described as these may vary. It is also to be understood that the terminology used herein is for the purpose of describing particular embodiments only, and is not intended to limit the scope of the present invention which will be limited only by the appended claims.

Throughout the description and claims of this specification, the word "comprise" and variations of the word, such as "comprising" and "comprises," means "including but not limited to," and is not intended to exclude, for example, other additives, components, integers or steps.

Those skilled in the art will recognize, or be able to ascertain using no more than routine experimentation, many equivalents to the specific embodiments of the method and compositions described herein. Such equivalents are intended to be encompassed by the following claims.

I claim:

1. A method of detecting a nucleotide variation within a nucleic acid of interest comprising:
    (a) a step comprising generating a set of extension products from a first nucleic acid and causing modified nucleotides to be present in the extension products, wherein the modified nucleotides comprise a single type of base,
    (b) a step comprising hybridizing the extension products to a second nucleic acid, (c) a step comprising contacting the hybridizing nucleic acid with one or more agents that collectively remove the modified nucleotides, (d) a step comprising contacting the hybridizing nucleic acid with a first enzyme that extends the extension products in the presence of three types of nuclease-resistant nucleotides and not in the presence of nucleotides that comprise the same type of base as the modified nucleotides, wherein each of the three types of nuclease-resistant nucleotides comprises a different type of base, (e) a step comprising contacting the hybridizing nucleic acid with a second enzyme that removes nucleotides from the 3' end of the extension products, wherein the second enzyme does not remove the nuclease-resistant nucleotides, (f) a step comprising contacting the hybridizing nucleic acid with a third enzyme that extends the extension products in the presence of nucleotides, (g) a step comprising distinguishing those extension products comprising a nuclease-resistant nucleotide from those extension products not comprising a nuclease-resistant nucleotide, wherein the first nucleic acid is a reference nucleic acid and the second nucleic acid is the nucleic acid of interest or wherein the first nucleic acid is the nucleic acid of interest and the second nucleic acid is a reference nucleic acid, thereby detecting nucleotide variation in the nucleic acid of interest.

2. The method of claim 1, wherein the reference nucleic acid comprises a wild-type sequence.

3. The method of claim 2, wherein the nucleic acid of interest comprises a sequence that corresponds to the wild-type sequence of the reference nucleic acid.

4. The method of claim 1, wherein in step (g) there are substantially no extension products not comprising a nuclease-resistant nucleotide, wherein distinguishing those extension products comprising a nuclease-resistant nucleotide from those extension products not comprising a nuclease-resistant nucleotide comprises detecting the presence of extension products.

5. The method of claim 1, wherein extension products are only present in step (g) if a nuclease-resistant nucleotide was incorporated into an extension product in step (d).

6. The method of claim 1, wherein a nuclease-resistant nucleotide is incorporated into an extension product in step (d) only if a nucleotide variation was present in the nucleic acid of interest.

7. The method of claim 1, wherein a nuclease-resistant nucleotide is incorporated into an extension product in step (d) substantially only if a nucleotide variation was present in the nucleic acid of interest.

8. The method of claim 1, wherein the nucleotide variation was present in the nucleic acid of interest at a site corresponding to the location of a modified nucleotide in the extension products.

9. The method of claim 1, nucleotides 5' of the nuclease-resistant nucleotide in the extension products are protected from removal by the second enzyme.

10. The method of claim 1, wherein extension products in which no nuclease-resistant nucleotide is present are digested by the second enzyme.

11. The method of claim 1, wherein the first nucleic acid comprises a primer sequence, wherein at least some of the extension products in which a nuclease-resistant nucleotide is present are extended in step (f) at least to the primer sequence in the first nucleic acid.

12. The method of claim 1, wherein the modified nucleotide is 7,8-dihydro-8-oxoguanine (8-oxoguanine), 8-oxoadenine, fapy-guanine, methyl-fapy-guanine, fapy-adenine, aflatoxin $B_1$-fapy-guanine, 5-hydroxy-cytosine, 5-hydroxy-uracil, ring-opened N-7 guanine adducts (7-methylguanine), ribose, uracil, or a combination.

13. The method of claim 1, wherein steps (c) and (d) are performed simultaneously.

14. The method of claim 1, wherein the one or more of the agents removes the base from the modified nucleotides.

15. The method of claim 1, wherein the one or more agents comprise an endonuclease.

16. The method of claim 1, wherein the one or more agents comprise Endonuclease IV.

17. The method of claim 1, wherein the one or more agents comprise formamidopyrimidine-DNA glycosylase (FPG).

18. The method of claim 1, wherein the first enzyme replaces the modified nucleotide with a labeled nucleotide.

19. The method of claim 1, wherein the first enzyme comprises a polymerase.

20. The method of claim 1, wherein the first enzyme is DNA polymerase.

21. The method of claim 1, wherein the first enzyme is a thermostable polymerase.

22. The method of claim 1, wherein the nuclease-resistant nucleotides comprise thio-modified deoxynucleotides.

23. The method of claim 1, wherein the nuclease-resistant nucleotides comprise borano-modified nucleotides.

24. The method of claim 1, wherein the second enzyme comprises an exonuclease.

25. The method of claim 1, wherein the second enzyme comprises Exonuclease III.

26. The method of claim 1, wherein the extension products are distinguished by real time PCR (rtPCR).

27. The method of claim 26, wherein PCR is mediated by two or more primers, wherein one or more of the primers comprises a fluorescent label.

28. The method of claim 27, wherein one or more of the primers comprises a fluorescent change primer.

29. The method of claim 1, wherein extension of the extension products in step (f) incorporates one or more labeled nucleotides into the extension products.

30. The method of claim 29, wherein one or more of the labeled nucleotides comprises biotin.

31. The method of claim 30, wherein the extension products are distinguished by detecting the labeled nucleotides.

32. The method of claim 1, wherein the extension products are distinguished via probe hybridization, primer extension, or a combination.

33. The method of claim 1, wherein the extension products are distinguished via association of the extension products with a solid support.

34. The method of claim 1, further comprising performing steps (a) through (g) one or more additional times each time using a different type of modified nucleotide comprising a different type of base.

35. The method of claim 1, wherein steps (a) through (g) are performed at least once using each of four different modified nucleotides, wherein each of the four different modified nucleotides comprises a different one of the four types of base.

36. The method of claim 1, further comprising sequencing the extension products with a nucleotide variation and comparing that sequence to a reference sequence, thereby specifically identifying the nucleotide variation in the first nucleic acid.

37. The method of claim 1, wherein the nucleotide variation is a single nucleotide variation.

38. The method of claim 1, wherein the nucleotide variation detected is a nucleotide variation in a single nucleotide.

39. The method of claim 1, wherein the extension products are labeled with a detectable label and the distinguishing step (g) comprises performing gel electrophoresis of the reaction from step (f), wherein the electrophoresis is of sufficient resolution to distinguish between a labeled extension product that is not further extended and a full length nucleic acid.

40. The method of claim 1, where modified nucleotides are caused to be present in the extension products by generating the extension products in the presence of modified nucleotides comprising a single type of base, wherein the extension products incorporate the modified nucleotides.

41. The method of claim 1, wherein modified nucleotides are caused to be present in the extension products by modifying nucleotides in the extension products to produce the modified nucleotides.

42. The method of claim 41, wherein nucleotides are modified in the extension products selectively.

43. The method of claim 41 or 42, wherein nucleotides are modified in the extension products in a limited way.

44. The method of claim 41, wherein nucleotides are modified in the extension products by chemical modification.

45. The method of claim 41, wherein nucleotides are modified in the extension products by enzymatic modification.

46. A method of detecting a nucleotide variation within a first nucleic acid comprising:
   a. a step comprising generating a set of extension products from a reference nucleic acid in the presence of modified nucleotides comprising a single type of base, wherein the extension products incorporate the modified nucleotides,
   b. a step comprising hybridizing the extension products to the first nucleic acid,
   c. a step comprising contacting the hybridizing nucleic acid with one or more agents that collectively remove the modified nucleotides,
   d. a step comprising contacting the hybridizing nucleic acid with a first enzyme that extends the extension products in the presence of three types of labeled nucleotides and not in the presence of nucleotides that comprise the same type of base as the modified nucleotides, wherein each of the three types of labeled nucleotides comprises a different type of base,
   e. a step comprising distinguishing those extension products comprising a labeled nucleotide from those extension products not comprising a labeled nucleotide, thereby detecting nucleotide variation in the first nucleic acid.

* * * * *

SEQUENCE LISTING

```
<160> NUMBER OF SEQ ID NOS: 3

<210> SEQ ID NO 1
<211> LENGTH: 44
<212> TYPE: DNA
<213> ORGANISM: Artificial Sequence
<220> FEATURE:
<223> OTHER INFORMATION: Description of Artificial Sequence:
      Note=Synthetic Construct

<400> SEQUENCE: 1
ataggcgtac tggtggagta tttataaagg tttctctgag gtga                44

<210> SEQ ID NO 2
<211> LENGTH: 22
<212> TYPE: DNA
<213> ORGANISM: Artificial Sequence
<220> FEATURE:
<223> OTHER INFORMATION: Description of Artificial Sequence:
      Note=Synthetic Construct

<400> SEQUENCE: 2
cacctcataa atatttccaa ag                                       22

<210> SEQ ID NO 3
<211> LENGTH: 23
<212> TYPE: DNA
<213> ORGANISM: Artificial Sequence
<220> FEATURE:
<223> OTHER INFORMATION: Description of Artificial Sequence:
      Note=Synthetic Construct

<400> SEQUENCE: 3
cacctcataa actatttcca aag                                      23
```